US009492562B2

(12) United States Patent
Tavernier et al.

(10) Patent No.: US 9,492,562 B2
(45) Date of Patent: Nov. 15, 2016

(54) TARGETED HUMAN-INTERFERON FUSION PROTEINS

(71) Applicants: VIB VZW, Ghent (BE); Universiteit Gent, Ghent (BE); Centre National de la Recherche Scientifique, Paris (FR); Universite Montpellier 2, Montpellier (FR); Centre Hospitalier Regional Universitaire de Montpellier, Montpellier (FR); Universitat Osnabruck, Osnabrück (DE)

(72) Inventors: Jan Tavernier, Balegem (BE); Gilles Uzé, Montpellier (FR); Guillaume Cartron, Combaillaux (FR); Franciane Paul, Montpellier (FR); Jacob Piehler, Osnabrück (DE)

(73) Assignees: VIB VZW, Ghent (BE); UNIVERSITEIT GENT, Ghent (BE); CENTRE NATIONAL DE LA RECHERCHE SCIENTIFIQUE (CNRS), Paris (FR); UNIVERSITE MONTPELLIER 2, Montpellier (FR); CENTRE HOSPITALIER REGIONAL UNIVERSITAIRE DE MONTPELLIER, Montpellier (FR); UNIVERSITAT OSNABRUCK, Osnabrück (DE)

( * ) Notice: Subject to any disclaimer, the term of this patent is extended or adjusted under 35 U.S.C. 154(b) by 48 days.

(21) Appl. No.: 14/372,730

(22) PCT Filed: Jan. 17, 2013

(86) PCT No.: PCT/EP2013/050787
§ 371 (c)(1),
(2) Date: Jul. 16, 2014

(87) PCT Pub. No.: WO2013/107791
PCT Pub. Date: Jul. 25, 2013

(65) Prior Publication Data
US 2014/0348789 A1 Nov. 27, 2014

(30) Foreign Application Priority Data
Jan. 20, 2012 (EP) .................................... 12305075

(51) Int. Cl.

| | |
|---|---|
| *A61K 38/21* | (2006.01) |
| *A61K 39/395* | (2006.01) |
| *A61K 45/00* | (2006.01) |
| *A61K 47/48* | (2006.01) |
| *C07K 14/56* | (2006.01) |
| *C07K 16/28* | (2006.01) |
| *C07K 16/32* | (2006.01) |

(52) U.S. Cl.
CPC ....... *A61K 47/48423* (2013.01); *A61K 38/212* (2013.01); *C07K 14/56* (2013.01); *C07K 16/2827* (2013.01); *C07K 16/2869* (2013.01); *C07K 16/2878* (2013.01); *C07K 16/32* (2013.01); *C07K 2317/569* (2013.01); *C07K 2317/622* (2013.01); *C07K 2319/31* (2013.01); *C07K 2319/74* (2013.01)

(58) Field of Classification Search
None
See application file for complete search history.

(56) References Cited

U.S. PATENT DOCUMENTS

| | | | | |
|---|---|---|---|---|
| 5,914,254 | A | 6/1999 | Mascarenhas et al. | |
| 8,980,267 | B2 | 3/2015 | Grewal et al. | |
| 9,139,634 | B2 | 9/2015 | Morrison et al. | |
| 2010/0172868 | A1 | 7/2010 | Morrison et al. | |
| 2010/0297076 | A1 | 11/2010 | Morrison et al. | |
| 2011/0081341 | A1* | 4/2011 | Honjo | A61K 31/7088 424/133.1 |
| 2011/0104112 | A1 | 5/2011 | Morrison et al. | |
| 2011/0274658 | A1 | 11/2011 | Silver et al. | |
| 2013/0183298 | A1 | 7/2013 | Le et al. | |
| 2015/0139951 | A1 | 5/2015 | Grewal et al. | |

FOREIGN PATENT DOCUMENTS

| | | | |
|---|---|---|---|
| WO | 9102754 | A1 | 3/1991 |
| WO | 2006053883 | A1 | 5/2006 |
| WO | 2006115800 | A2 | 11/2006 |
| WO | 2008014612 | A1 | 2/2008 |
| WO | 2008124086 | A2 | 10/2008 |
| WO | 2009003145 | A1 | 12/2008 |

(Continued)

OTHER PUBLICATIONS

Bork, 2000, Genome Research 10:398-400.*

(Continued)

*Primary Examiner* — Christine J Saoud
*Assistant Examiner* — Jegatheesan Seharaseyon
(74) *Attorney, Agent, or Firm* — Morgan, Lewis & Bockius LLP

(57) ABSTRACT

This disclosure relates to a modified α-helical bundle cytokine, with reduced activity via an α-helical bundle cytokine receptor, wherein the α-helical bundle cytokine is specifically delivered to target cells. Preferably, the α-helical bundle cytokine is a mutant, more preferably it is a mutant interferon, with low affinity to the interferon receptor, wherein the mutant interferon is specifically delivered to target cells. The targeting is realized by fusion of the modified α-helical bundle cytokine to a targeting moiety, preferably an antibody. This disclosure relates further to the use of such targeted modified α-helical bundle cytokine to treat diseases. A preferred embodiment is the use of a targeted mutant interferon, to treat diseases, preferably viral diseases and tumors.

4 Claims, 16 Drawing Sheets

(56) References Cited

FOREIGN PATENT DOCUMENTS

| WO | 2009039409 A1 | 3/2009 |
|---|---|---|
| WO | 2010036918 A2 | 4/2010 |
| WO | 2010066740 A1 | 6/2010 |
| WO | 2011020783 A2 | 2/2011 |
| WO | 2011029870 A1 | 3/2011 |
| WO | 2012170072 A1 | 12/2012 |
| WO | 2013059885 A2 | 5/2013 |
| WO | 2013107791 A1 | 7/2013 |
| WO | 2013134138 A1 | 9/2013 |

OTHER PUBLICATIONS

Bork et al., 1996, Trends in Genetics 12:425-427.*
Wells, 1990, Biochemistry 29:8509-8517.*
Ngo et al., 1994, The Protein Folding Problem and Tertiary Structure Prediction, pp. 492-495.*
Masci et al., New and Modified Interferon alfas: Preclinical and Clinical Data, Current Oncology Reports, Mar. 1, 2003, vol. 5, No. 2.
Roisman et al., Structure of the interferon-receptor complex determined by distance constraints from double-mutant cycles and flexible docking, Proceedings of the National Academy of Sciences, Nov. 6, 2001, pp. 13231-13236, vol. 98, No. 23.
Coulstock et al., Liver-targeting of interferon-alpha with tissue-specific domain antibodies, PLOS One, Feb. 2013, pp. 1-11, vol. 8, No. 2.
PCT International Search Report, PCT/EP2013/050787, dated Jun. 14, 2013.
Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.
Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.
Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, (1993), pp. 8749-8757.
de Bruyn, M., et al., "Antibody-Based Fusion Proteins to Target Death Receptors in Cancer", Cancer Letters, vol. 332, (2013), pp. 175-183.
Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garcin, G., et al., "High Efficiency Cell-Specific Targeting of Cytokine Activity", Nature Communications, (2014), pp. 1-9.
Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Pan, M., et al., "Mutation of the INFAR-1 Receptor Binding Site of Human IFN-[alpha]2 Generates Type I IFN Competitive Antagonists", Biochemistry, vol. 47, (2008), pp. 12018-12027.
Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.
Rafei, M., et al., "A MCP1 Fusokine with CCR2-Specific Tumoricidal Activity", Molecular Cancer, vol. 10, No. 121, (2011), pp. 1-11.
Ratei, M., et al., "An Engineered GM-CSF-CCL2 Fusokine is a Potent Inhibitor of CCR2-Driven Inflammation as Demonstrated in a Murine Model of Inflammatory Arthritis", The Journal of Immunology, vol. 183, (2009), pp. 1759-1766.
Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.
Schutyser, E., et al., "The CC Chemokine CC20 and its Receptor CCR6", Cytokine & Growth Factor Reviews, vol. 14, (2003), pp. 409-426.
Weber, H., et al., "Single Amino Acid Changes that Render Human IFN-[alpha]2 Biologically Active on Mouse Cells", The EMBO Journal, vol. 6, No. 3, (1981), pp. 591-598.

* cited by examiner

STAT1-phospho

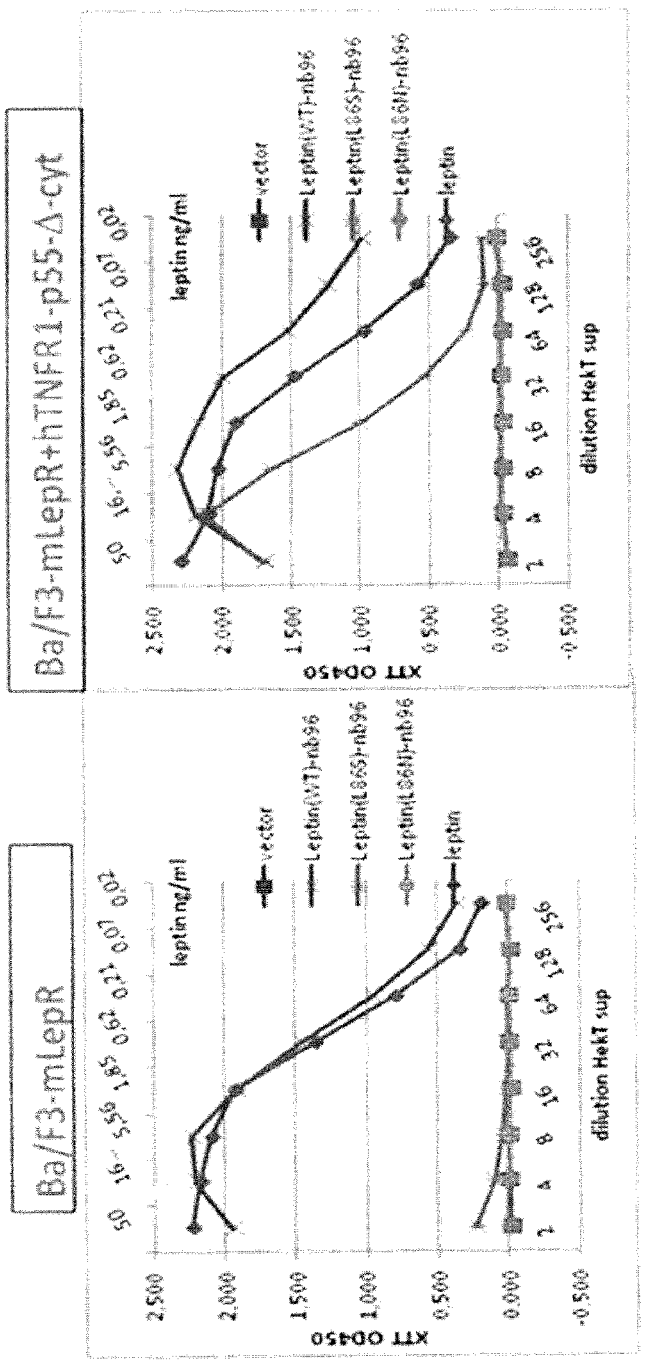
FIG. 16cont.

H6-Leptin construct

| sIgκ | H6-leptin | (GGS)20 | Nb96-H6 (anti-hp55) |

HHHHHHGGSGIQKVQDDTKTLIKTIVTRINDISHTQSVSAKQRVTGLDFIPGLHPILSLSKMDQTLAVYQQVLTSLPSQN
VLQIANDLENLRDL[86]LHLLAFSKSCSLPQTSGLQKPESLDGVLEASLYSTEVVALSRLQGSLQDILQQLDVSPECALDGG
SGGSGGSGGSGGSGGSGGSGGSGGSGGSGGSGGSGGSGGSGGSGGSGGSGGSGGSSGSMAQVQLQESGGGV
VQPGGSLTLSCTRTGFTASTNAVGWYRQGPGKKCEWVSYMTIPSGRTTYADAVKGRFAMSRDKAKSTVFLQMNSLKP
EDTAVYYCGDVPFSTLPAMCTNDGPWGQGTQVTVSSHHHHHH (SEQ ID NO: 9)

Mleptin construct

| sigPEP-mLeptin | mleptin | (GGS)20 | Nb96-H6 (anti-hp55) |

GGSGIQKVQDDTKTLIKTIVTRINDISHTQSVSAKQRVTGLDFIPGLHPILSLSKMDQTLAVYQQVLTSLPSQNVLQIANDL
ENLRDL[86]LHLLAFSKSCSLPQTSGLQKPESLDGVLEASLYSTEVVALSRLQGSLQDILQQLDVSPECALDGGSGGSGGS
GGSGGSGGSGGSGGSGGSGGSGGSGGSGGSGGSGGSGGSGGSGGSSGSMAQVQLQESGGGVVQPGGSL
TLSCTRTGFTASTNAVGWYRQGPGKKCEWVSYMTIPSGRTTYADAVKGRFAMSRDKAKSTVFLQNSLKPEDTAVYYCG
DVPFSTLPAMCTNDGPWGQGTQVTVSSHHHHHH (SEQ ID NO: 10)

FIG. 17

TARGETED HUMAN-INTERFERON FUSION PROTEINS

CROSS-REFERENCE TO RELATED APPLICATIONS

This application is a national phase entry under 35 U.S.C. §371 of International Patent Application PCT/EP2013/050787, filed Jan. 17, 2013, designating the United States of America and published in English as International Patent Publication WO 2013/107791 A1 on Jul. 25, 2013, which claims the benefit under Article 8 of the Patent Cooperation Treaty to European Patent Application Serial No. 12305075.9, filed Jan. 20, 2012.

TECHNICAL FIELD

The disclosure described herein relates to a modified α-helical bundle cytokine, with reduced activity via an α-helical bundle cytokine receptor, wherein the α-helical bundle cytokine is specifically delivered to target cells. Preferably, the α-helical bundle cytokine is a mutant, more preferably, it is a mutant interferon, with low affinity to the interferon receptor, wherein the mutant interferon is specifically delivered to target cells. The targeting is realized by fusion of the modified α-helical bundle cytokine to a targeting moiety, preferably an antibody. This disclosure relates further to the use of such targeted modified α-helical bundle cytokine to treat diseases. A preferred embodiment is the use of a targeted mutant interferon to treat diseases, preferably viral diseases and tumors.

BACKGROUND

Cytokines are small proteins that play an important role in intercellular communication. Cytokines can be classified based on their structure, the largest group being the four-α-helix bundle family. This family can, based on the use of receptors, further be divided into the interferon (IFN) and interleukin (IL)-2, -3, -10 and -12 subfamilies. The α-helical bundle cytokines are important as possible biopharmaceuticals for treatment of human diseases. As non-limiting examples, erythropoietin is used for treatment of anemia or red blood cell deficiency, somatotropin for treatment of growth hormone deficiency, and interleukin-2 in the treatment of cancer.

Within the α-helical bundle cytokines, type I IFNs belong to a cytokine family having important biological functions. In humans, there are 17 different type I IFNs (13α, β, ϵ, κ, ω), which signal through a ubiquitously expressed cell surface receptor composed of two chains IFNAR1 and IFNAR2. The assembling of the IFN-receptor complex initiates the activation of several signal transduction pathways that, depending upon the cell type, modify cellular differentiation and/or functions.

By acting on virtually every cell type, type I IFN is able to prevent productive viral infection. In addition, it exhibits marked antiangiogenic and proapoptotic effects. Type I IFNs are also deeply implicated in the regulation of several functions of the innate and adaptive immunity, as well as on bone homeostasis. It acts particularly on the activation/differentiation of dendritic cells and osteoclasts. The type I IFN system is, in fact, critically important for the health of mammals.

Preclinical studies in mice have established a remarkable efficacy of type I IFN for the treatment of both viral or tumor diseases. Noteworthy, mice cured of an experimental tumor by IFN treatment have been found immunized against the initial tumor, suggesting that IFN acts not only to engage the processes of tumor rejection but also to break the immune tolerance against the tumor. Based on these studies, IFNα was approved in clinics for the treatment of both viral infection and cancer. More recently, IFNβ was shown to be effective in relapsing-remitting multiple sclerosis and was also approved for this pathology. Unfortunately, the clinical efficacy of IFN was often found disappointing and today, other therapeutic strategies such as specific antiviral compounds, chemotherapies and monoclonal antibodies have, when possible, largely supplanted IFN broad application. Today, IFN is the first line therapeutic choice for only HBV and HCV chronic infections and for a limited number of tumors.

The efficacy of type I IFN in clinical practice is limited by ineffective dosing due to significant systemic toxicity and side effects, including flu-like syndrome, depression, hepatotoxicity, autoimmune disease, thyroid dysfunction and weight loss. It would thus be highly worthwhile to target IFN activity toward only the cellular population that should be treated with IFN (e.g., infected organ or tumor mass) or activated by IFN (e.g., subsets of immune cells).

In order to solve or limit the systemic toxicity of cytokines, specific targeting of cytokines by antibody-cytokine fusion proteins has been proposed (Ortiz-Sanchez et al., 2008). Rossi et al. (2009) specifically disclose CD20-targeted tetrameric IFNα, and its use in B-cell lymphoma therapy. However, the fusion maintains its biological activity, and is even more active than commercial pegylated IFN, which means that the unwanted side effects in human treatment would still be present, or would even be more severe. WO2009039409 discloses targeted IFN and its apoptotic and anti-tumor activities. Not only does the patent application disclose the fusion of an antibody as targeting moiety with wild-type IFN, but also with mutated IFN. However, it is stated that the IFN fragment should retain its endogenous activity at a level of at least 80%, or even at a higher level than wild-type IFN. Also, in this case, the fusion is retaining the unwanted side effects of the wild-type.

SUMMARY OF THE DISCLOSURE

Surprisingly, it was found that a modified α-helical bundle cytokine, with a decreased affinity for the α-helical bundle cytokine receptor and a consequent decreased specific bioactivity, can be fused to a targeting moiety, wherein the bioactivity is restored toward the targeted cells, but not toward cells that are not targeted by the construct. Such construct has the advantage over the art of having less side effects, especially a lower systemic toxicity, while retaining the bioactivity against the target cells.

A first aspect of this disclosure is a targeting construct comprising modified α-helical bundle cytokine, characterized by a reduced affinity for the α-helical bundle cytokine receptor, and a targeting moiety. α-helical bundle cytokines are known to the person skilled in the art and include, but are not limited to, Cardiotrophin-like cytokine NNT-1, Ciliary neurothrophic factor, Macrophage colony stimulating factor, Granulocyte-macrophage colony stimulating factor, Granulocyte colony stimulating factor, Cardiotrophin-1, Erythropoietin, FLT3 ligand, Somatotropin, Interferon α-1, 2, 4, 5, 6, 7, 8, 10, 13, 14, 16, 17, 21, Interferon β, Interferon γ, Interferon κ, Interferon ϵ, Interferon τ-1, Interferon ω-1, Interleukin 2, 3, 4, 5, 6, 7, 9, 10, 11, 12 α chain, 13, 15, 19, 20, 21, 22, 23, 24, 26, 27, 28A, 29, 31, Stem cell factor, Leptin, Leukemia inhibitor factor, Oncostatin M, Prolactin, and Thrombopoietin. For a review on α-helical bundle cytokines, see Conklin (2004). A modified α-helical bundle cytokine means that the α-helical bundle cytokine has been changed to alter the affinity to the receptor, with a final result that the modified α-helical bundle cytokine has a reduced affinity for the receptor and a consequent reduced biological activity, as compared to the endogenous wild-type cytokine that binds normally to the receptor. Such a modification can be a modification that decreases the activity of the normal wild-type cytokine, or it can be a modification that increases the affinity of a homologous, non-endogenous α-helical bundle cytokine (such as, but not limited to, a mouse α-helical bundle cytokine, binding to a human α-helical bundle cytokine receptor). Modifications can be any modification reducing or increasing the activity known to the person skilled in the art including, but not limited to, chemical and/or enzymatic modifications such as pegylation and glycosylation, fusion to other proteins and mutations. Preferably, the modification is a mutation. Even more preferably, it is a mutation decreasing the affinity of the-α-helical bundle cytokine. A "reduced affinity" and a "consequent reduced biological activity," as used herein, means that the modified α-helical bundle cytokine has a biological activity of less than 70% of the biological activity of the α-helical bundle cytokine; even more preferably, less than 60% of the biological activity of the α-helical bundle cytokine; more preferably, less than 50% of the biological activity of the α-helical bundle cytokine; more preferably, less than 40% of the biological activity of the α-helical bundle cytokine; more preferably, less than 30% of the biological activity of the α-helical bundle cytokine; more preferably, less than 20% of the biological activity of the α-helical bundle cytokine; and most preferably, less than 10% of the biological activity of the α-helical bundle cytokine as compared to the α-helical bundle cytokine that normally binds to the receptor. Preferably, the modified α-helical bundle cytokine is a mutant of the wild-type α-helical bundle cytokine and the activity is compared with the wild type α-helical bundle cytokine. The affinity and/or the activity can be measured by any method known to the person skilled in the art. Preferably, the activity is measured by measuring and quantifying STAT phosphorylation.

A preferred embodiment of the disclosure is a targeting construct comprising a mutant IFN characterized by reduced affinity for the IFN receptor and a targeting moiety. IFN can be any IFN including, but not limited to, IFNα, IFNβ and ω. A "mutant IFN," as used herein, can be any mutant form that has a lower affinity for the receptor and, as a consequence, a lower antiproliferative activity and/or a lower antiviral activity. Indeed, as shown by Piehler et al. (2000), the relative affinity correlates directly with the relative antiproliferative activity and with the relative antiviral activity. The affinity of the mutant IFN to the receptor, in comparison to the affinity of the wild-type IFN to the receptor, can be measured by reflectometric interference spectroscopy under flow-through conditions, as described by Brecht et al. (1993). The mutant may be a point mutant, a deletion or an insertion mutant, or a combination thereof. Preferably, the mutant IFN is obtained by active mutagenesis, such as, but not limited to, site-directed mutagenesis by polymerase chain reaction amplification. Preferably, the mutant IFN has a biological activity of less than 70% of the biological activity of the wild-type IFN; even more preferably, less than 60% of the biological activity of the wild-type IFN; more preferably, less than 50% of the biological activity of the wild-type IFN; more preferably, less than 40% of the biological activity of the wild-type IFN; more preferably, less than 30% of the biological activity of the wild-type IFN; more preferably, less than 20% of the biological activity of the wild-type IFN; most preferably, less than 10% of the biological activity of the wild-type of which it is deduced (i.e., the wild-type IFN of which the coding sequence has been mutated to obtain the mutant IFN). Mutant forms of IFN are known to the person skilled in the art. As a non-limiting example, IFNα2 mutants have been listed in Piehler et al. (2000). Preferably, the IFN is a type I IFN. Even more preferably, the mutant is an IFNα; even more preferably, the mutant is an IFNα2. More preferably, the IFNα2 mutant is mutated in one or more amino acids of the region 144-154, preferably at positions 148, 149 and/or 153; even more preferably, the mutant IFNα2 is selected from the group consisting of IFNα2 L153A, IFNα2 R149A and IFNα2 M148A. Most preferably, the mutant is selected from the group consisting of IFNα2 L153A and IFNα2 R149A.

Preferably, the receptor is IFNAR2.

Preferably, the targeting moiety is targeting to a marker expressed on an IFN receptor-expressing cell, preferably a cell expressing IFNAR2. In one preferred embodiment, the targeting moiety is directed to a tissue-specific marker. Preferably, the tissue is a cancer tissue. The cancer can be any cancer including, but not limited to, B cell lymphoma, lung cancer, breast cancer, colorectal cancer or prostate cancer. In another preferred embodiment, the targeting moiety is directed to a marker selected from the group consisting of Her2 and CD20. In still another preferred embodiment, the targeting moiety is directed to a cell surface marker specific for viral infected cells such as, but not limited to, influenza M2 protein, LMP1 and EBV proteins). In still another embodiment, the targeting moiety is directed toward an osteoclast marker such as DC-STAMP or RANK. Indeed, it is known that IFN-β plays an important role in bone homeostasis, regulated by RANK and IFNAR coexpressing cells (Abraham et al., 2009). In still another embodiment, the targeting moiety is directed toward a marker specifically expressed on the surface of an immune cell type on which IFN may regulate activity and/or differentiation. The marker PDL2 specifically expressed on dendritic cells and some immune cells is an example.

A targeting moiety, as used here, can be a protein as a part of a specifically binding protein complex, or any specifically binding protein or protein fragment, known to the person skilled in the art. It includes, but is not limited to, carbohydrate binding domains (CBD) (Blake et al., 2006), lectin binding proteins, heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO2010066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009). Preferably, the targeting moiety consists of a single polypeptide chain and is not post-translationally modified. Even more preferably, the targeting moiety is a nanobody.

The targeting construct can be any targeting construct known to the person skilled in the art. As a non-limiting example, the targeting moiety may be chemically linked to the mutant interferon, or it may be a recombinant fusion protein. Preferably, the targeting construct is a recombinant fusion protein. The targeting moiety may be fused directly to the mutant IFN, or it may be fused with the help of a linker fragment. The targeting moiety may be fused at the amino-terminal or at the carboxyterminal end of the mutated IFN;

preferably, the targeting moiety is fused at the amino-terminal extremity of the mutated IFN molecule.

Another aspect of the disclosure is a targeting construct according to the disclosure for use as a medicament.

Still another aspect of the disclosure is the use of a targeting construct according to the disclosure for the manufacture of a medicament to treat cancer.

Still another aspect of the disclosure is the use of a targeting construct according to the disclosure for the manufacture of a medicament to treat a viral disease. As a non-limiting example, the viral disease may be HIV infection, HBV infection or HCV infection.

Another aspect of the disclosure is a targeting construct according to the disclosure for use in treatment of cancer.

Still another aspect of the disclosure is a targeting construct according to the disclosure for use in treatment of a viral disease. As a non-limiting example, the viral disease may be HIV infection, HBV infection or HCV infection.

Still another aspect of the disclosure is a targeting construct according to the disclosure for use in treatment of diseases involving bone degradation, such as, but not limited to, osteoporosis.

Still another aspect of the disclosure is a pharmaceutical composition comprising a targeting construct according to the disclosure and a suitable excipient. It is clear for the person skilled in the art that such a pharmaceutical composition can be used alone, or in a combination treatment, such as, but not limited to, a combination with chemotherapy.

BRIEF DESCRIPTION OF THE DRAWINGS

FIG. 4A, Quantification of their specific activities on cells expressing the target (HL116-mLR) or on cells lacking the target (HL116). FIG. 4B, Calculation of the targeting efficiencies of the different constructs.

FIG. 8A, Cytopathic effect of the EMCV on HL116 cells (dark gray symbols) or on HL116-mLR (light grey symbols) of parental IFNA2 (upper left panel) or of the 4-11-IFNA2-R149A (lower left panel). FIG. 8B, Upper panel: calculated EC50 for antiviral activity; lower panel: calculated targeting efficiencies.

FIG. 9B) on BXPC3 and BT474 cell lines, which express different number of Her2 molecule at their surface ($10.9 \times 10^3$ and $478 \times 10^3$, respectively). The ordinate scale of FIG. 9A cannot be compared to the ordinate scale of FIG. 9B.

FIG. 17: construction of the targeted leptin constructs (SEQ ID NOS:9 and 10).

DETAILED DESCRIPTION

Examples

Figure 1:
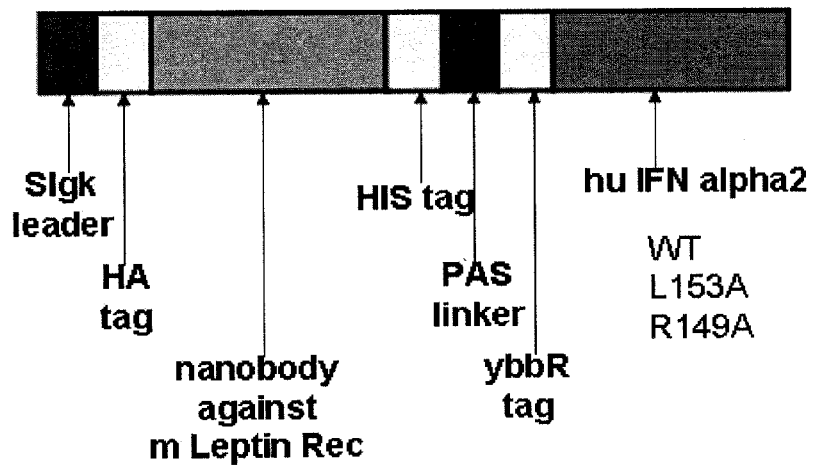
FIG. 1: Representation of the structural elements of the nanobody-IFN fusion protein.

Materials and Methods to the Examples
Nanobodies and ScFv

The nanobody 4-11 directed against the murine leptin receptor was described in Zabeau et al. (2012), and in the patent application WO 2006/053883. Its coding sequence is cloned into the mammalian expression vector pMET7 (Takebe et al., 1988) in fusion with the SIgk leader peptide, the HA tag and albumin. Plasmid name: pMET7 SIgK-HA-4.11-Albumin.

The nanobody 4-10 is also described in Zabeau et al. (2012).

The anti Her2 nanobodies 1R59B and 2R5A are described in Vaneycken et al. (2011). They were fused to the human IFNA2-Q124R and to the human IFNA2-R149A in the pMET7 vector. Fusion protein was produced by transfection of 293T cells.

The anti PD-L2 nanobody 122 was from Johan Grooten (VIB, Gent, Belgium). It was fused to the human IFNA2-Q124R in the pMET7 vector. The fusion protein was produced by transfection of 293T cells and purified using the HisPur Ni-NTA purification kit (Pierce, Thermo Scientific).

The anti TNF nanobody was obtained from Claude Libert (VIB).

The anti Her2 ScFv was obtained from Andrea Plückthun (Wörn et al., 1998). It was fused to the human IFNA2-Q124R in the pMET7 vector. The fusion protein was produced by transfection of 293T cells.

Control nanobody against GFP was obtained from Katrien Van Impe (University Ghent).

Interferons

The IFNα2 and the mutants L153A and R149A, which show an IFNAR2 affinity reduced by a factor 10 and 100, respectively, have been described in Roisman et al. (2001). IFN coding sequences are cloned in the pT3T7 vector (Stratagene) in fusion with the ybbR tag. Plasmid names: pT7T3ybbR-IFNa2, pT7T3ybbR-IFNa2-L153A, pT7T3ybbR-IFNa2-R149A.

The human IFNA2 Q124R has a high affinity for the murine IFNAR1 chain and a low affinity for the murine IFNAR2 chain. (Weber et al., 1987.)

Nanobody-IFN Fusion Construction

The coding sequence of the IFNα2, wild-type, L153A and R149A were synthesized by PCR from the corresponding pT3T7ybbR IFNa2 plasmids using the Expand High Fidelity PCR system from Roche Diagnostics and the following primers: Forward: 5'GGGGGGTCCGGACCATCACCAT-CACCATCACCATCACCATCACCCTGCTTCTCCCGCC TCCCCAGCATCACCTGCCAGCCCAGCAAGTGA-TAGCCTGGAATTTATTGC3' (SEQ ID NO: 1), Reverse: 5' CGTCTAG ATCATTC CTTACTTCTTAAAC3' (SEQ ID NO: 2). This PCR introduces a His tag and a series of five Proline-Alanine-Serine (PAS) repeats at the amino terminal extremity of the IFNs. The PCR products were digested with BspEI and XbaI and cloned into BspEI-XbaI digested pMET7 SIgK-HA-4.11-Albumin vector to obtain pMET7 SIgK-HA-4.11-His-PAS-ybbr-IFNA2, pMET7 SIgK-HA-4.11-His-PAS-ybbr-IFNA2-L153A and pMET7 SIgK-HA-4.11-His-PAS-ybbr-IFNA2-R149A.

In a similar way, the human mutant Q124R was fused to the 1R59B nanobody and to the anti-PD-L2 nanobody.

Production of the Nanobody-IFN Fusion Protein

HEK293T cells were grown in DMEM supplemented with 10% FCS. They were transfected with pMET7 SIgK-HA-4.11-His-PAS-ybbr-IFNA2, pMET7 SIgK-HA-4.11-His-PAS-ybbr-IFNA2-L153A pMET7 SIgK-HA-4.11-His-PAS-ybbr-IFNA2-R149A, pMET7 SIgK-HA-2R5A-His-PAS-ybbr-IFNA2-R149A, pMET7 SIgK-HA-1R59B-His-PAS-ybbr-IFNA2-Q124R, pMET7 SIgK-HA-4D5-His-PAS-ybbr-IFNA2-Q124R or pMET7 SIgK-HA-122-His-PAS-ybbr-IFNA2-Q124R using lipofectamin (Invitrogen). 48 hours after the transfection, culture mediums were harvested and stored at −20° C.

Alternatively, sequences encoding the different nanobody-IFN fusions were subcloned into the baculovirus transfer plasmid pBAC-3 (Novagen). Proteins were produced by insect cells using the BacVector kit (Novagen) and purified to homogeneity using the HisPur Ni-NTA purification kit (Pierce, Thermo Scientific) and gel filtration. Protein concentrations were measured by absorbance at 280 nm.

IFN Reporter Cell Lines

The HL116 clone (Uzê et al., 1994) is derived from the human HT1080 cell line. It contains the firefly luciferase gene controlled by the IFN-inducible 6-16 promoter. The HL116 cells were co-transfected with an expression vector encoding the short isoform of the murine leptin receptor (pMET7 mLRsh-FLAG, Eyckerman et al., 1999) and pSV2neo (Southern and Berg 1982). Stable transfected clones were isolated in G418-containing medium. The clone 10 was selected after analysis of the surface expression level of the murine leptin receptor by FACS, using the biotinylated anti-mouse leptin receptor antibody BAF497 from R&D and streptavidin-APC (BD Bioscience).

HT1080 cells were cotransfected with p6-16-RL, a plasmid encoding the Renilla luciferase (from pRL-null, Promega) controlled by the IFN-inducible 6-16 promoter (from p1.8gpt-5, Pellegrini et al., 1989), pBB3 (Bourachot et al., 1982) and salmon sperm DNA (Sigma). Stable transfected clones were isolated in HAT-containing medium. The clone 4 was selected for a high level of renilla luciferase activity induction upon IFN induction.

The human pancreatic carcinoma BXPC3 (Tan et al., 1986; ATCC: CRL 1687) and breast cancer BT474 (Lasfargues et al., 1979; ATCC: HTB-20) cell lines were obtained from ATCC.

The mouse BTG9A cells were described in Uzê et al. (1990).

Measurement of the Luciferase Activities

IFN-specific activities were measured by quantifying the luciferase activity induced in HL116 cells and on the HL116 clone 10 expressing the mLR. The EC50 were calculated using non-linear data regression with GraphPad Prism software.

Luciferase activities were determined on a Berthold centro LB960 luminometer using either the Firefly Luciferase Assay System or the Dual-Luciferase Reporter Assay System from Promega after six hours IFN stimulation.

Quantitative RT-PCR

The expression of the interferon inducible gene 6-16 was quantified by RT-PCR relative to GAPDH or β-actin. Cells were treated with targeted or control IFN for 4 hours. Total RNA was purified with RNEASY® columns (Qiagen). Reverse transcriptions were primed with random primers and performed using Moloney murine leukemia virus reverse transcriptase (Invitrogen). Quantitative real-time PCR (qRT-PCR) was performed using a LIGHTCYCLER® as described (Coccia et al., 2004).

For Her2, the transfection culture medium was assayed on murine BTG9A and BTG9A cells expressing human Her2 for expression of the OASL2 gene relatively to the expression of the β actin gene by quantitative RT-PCR using a Light Cycler (Roche) and the following primers: OASL2 forward: CAC-GAC-TGT-AGG-CCC-CAG-CGA (SEQ ID NO: 3); OASL2 reverse: AGC-AGC-TGT-CTC-TCC-CCT-CCG (SEQ ID NO: 4); βactin forward: AGA-GGG-AAA-TCG-TGC-GTG-AC (SEQ ID NO: 5); βactin reverse: CAA-TAG-TGA-TGA-CCT-GGC-CGT (SEQ ID NO: 6). In a similar way the ISG expression in Her2 targeted cells was measured using the same βactin primers and the following ISG15 primers: ISG15 forward: GAG-CTA-GAG-CCT-GCA-GCA-AT (SEQ ID NO: 7); ISG15 reverse: TTC-TGG-GCA-ATC-TGC-TTC-TT (SEQ ID NO: 8).

Antiviral Assay

The antiviral assay was performed using the EMC virus and scoring the virus replication-dependent cytopathic effect as described in Stewart (1979).

Measurement of her2 Phosphorylation

BTG9A cells expressing human Her2 were treated with 200 pM to 2 nM of 1 R59B-IFNA2-Q124R for 10 to 30 min. Cells were lysed in RIPA, and analysed by western blot on an ODYSSEY FC (gels imaging system using visible, near-infrared or chemiluminesce signals, Licor Bioscience) after 7% SDS-PAGE (40 µg lane). Phopho-Her2 was detected with the anti Her2 Y-P 1248 (Upstate #06-229) and the Goat anti rabbit secondary antibody IRDye 680 (Licor Bioscience #926-32221).

Measurement of STAT1 Phosphorylation

STAT1 phosporylated on Y701 were detected by FACS using the STAT1-PY701 (PE) (Beckton Dickinston #612564) and the manufacturer instruction for the PHOS-FLOW (flow cytometry-based protein phosphorylation detection) technology.

Targeted Leptin Constructs

The sequence of the targeted leptin constructs is given in FIG. 17. The L86 that is indicated is the amino acid that is mutated either to S or N.

Example 1

The Nanobody-Interferon Fusion Proteins

FIG. 1 shows a schematic representation of the nanobody-IFN fusion proteins constructed with either IFNα2 wild-type or the L153A and R149A mutants.

Example 2

Figure 2:
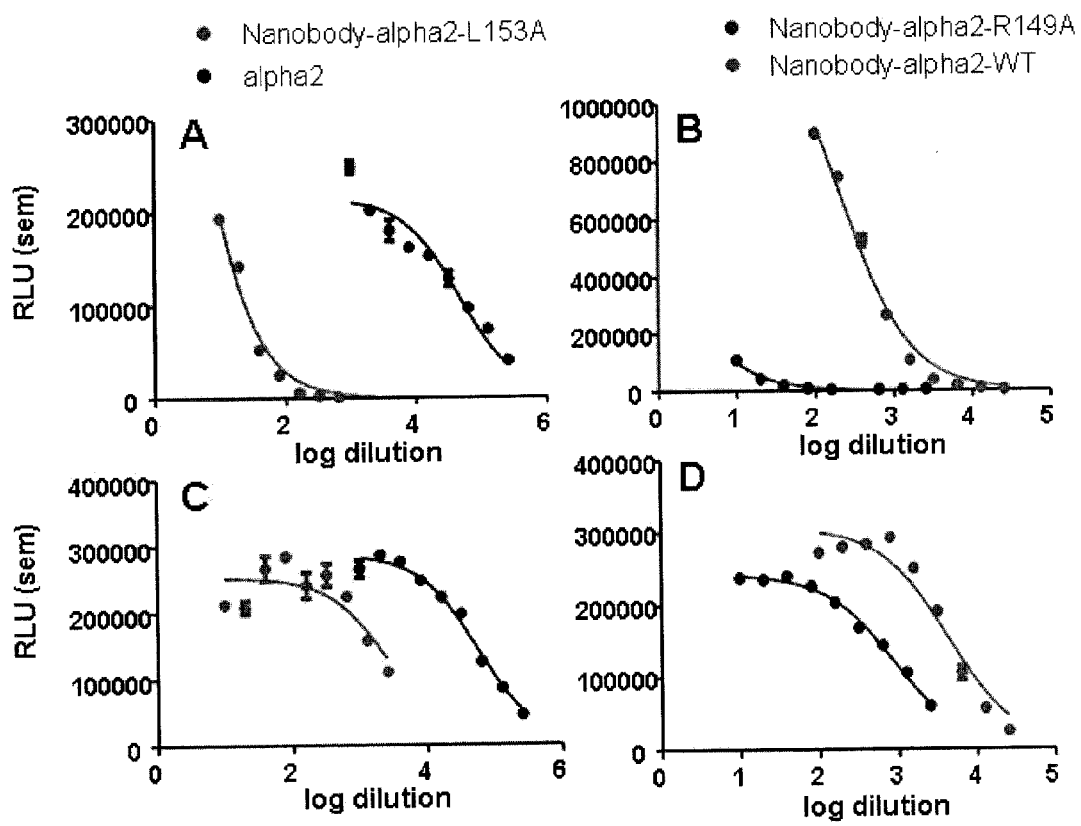
FIG. 2: Firefly luciferase activity induced by the indicated IFN preparation on HL116 cells (panels A and B) or HL116 cells expressing the murine leptin receptor (mLR) (panels C and D). Panels A and C on the one hand, and panels B and D on the other hand, were generated in two separate experiments. Consequently, only vertical comparison (panel A versus panel C or panel B versus panel D) is possible.

IFN Activity of the Nanobody-IFN Fusion Proteins is Targeted Toward Murine Leptin Receptor Expressing Cells The three nanobody fusion proteins with IFNα2 WT, IFNα2 L153A or R149A were assayed on both HL116 and HL116-mLR-clone 10 cells, which express the murine leptin receptor. The IFNα2 alone was also assayed in this assay system in order to check that the two cell clones do not differ in their IFN responsiveness. Indeed, both HL116 and HL116-mLR-clone 10 cells are equally sensitive to this IFN (FIGS. 2A and 2C, black symbols). The IFN activity of the three nanobody-IFN fusion proteins is, however, dramatically increased in cells expressing the leptin receptor compared to parental HL116 cells (compare FIG. 2A with FIG. 2C and FIG. 2B with FIG. 2D).

It was estimated that cells expressing the leptin receptor are 10-, 100- and 1000-fold more sensitive than parental HL116 cells to the nanobody-IFN WT, L153A and R149A, respectively. Since the affinities for IFNAR2 of the IFN mutant L153A and R149A are 0.1 and 0.01 relative to the WT, there is a correlation between the loss of activity caused by mutations in the IFNAR2 binding site and the targeting efficiency by the nanobody.

Figure 3:
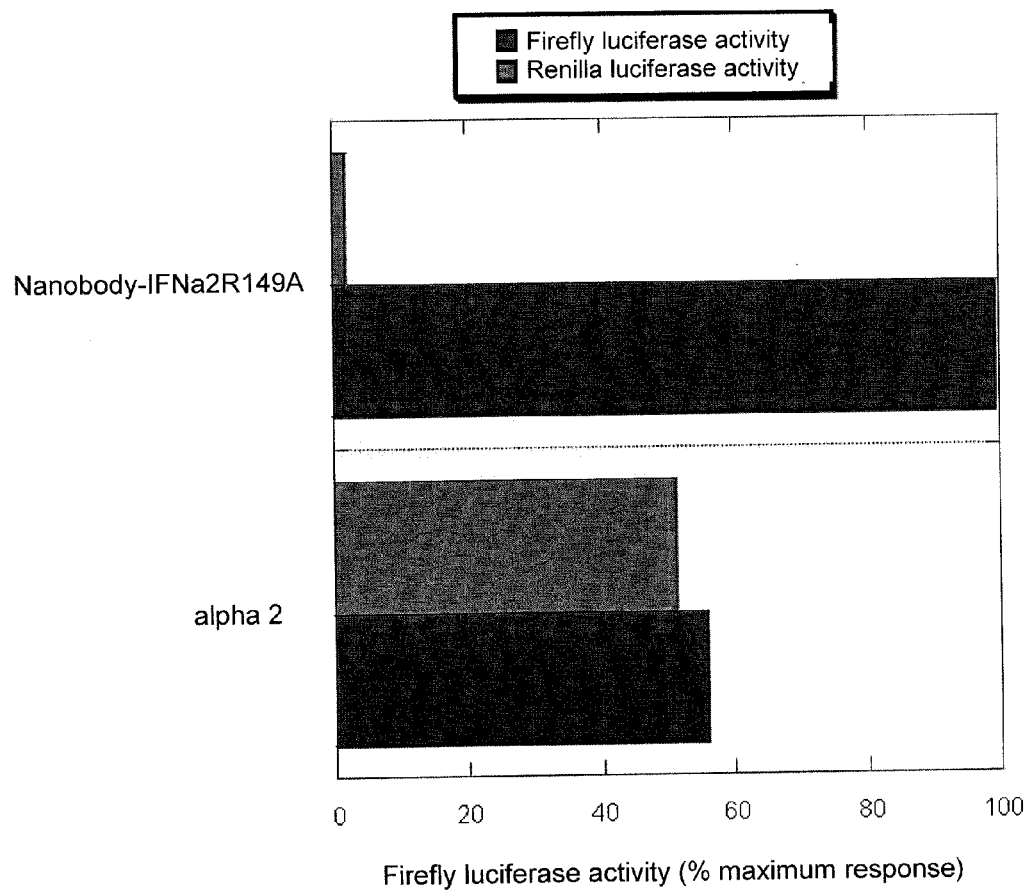
FIG. 3: Renilla (light grey) and Firefly (dark grey) luciferase activity induced by the nanobody-IFNα2R149A or by the IFNα2 (7 pM) in a 1:1 coculture of cells expressing the leptin receptor and an IFN-inducible firefly luciferase or in cells expressing an IFN-inducible renilla luciferase but devoid of leptin receptor. Luciferase activities are expressed as a percentage of the luciferase activities induced by 3 nM IFN α2.

In order to determine whether the IFN activity of the nanobody-IFN fusion proteins is delivered only on cells expressing the nanobody target or also on neighboring cells, the nanobody-IFNα2R149A was assayed on a coculture of HL116-mLR-clone10 and HT1080-6-16 renilla luciferase clone4. Both cell types will express luciferase activity in response to IFN stimulation, but cells expressing the target of the nanobody will display a firefly luciferase activity, whereas cells devoid of leptin receptor will display a renilla luciferase activity. The dilution of the nanobody-IFNα2R149A protein was chosen at 1/30, a dilution that induces a maximal response in cells carrying the leptin receptor and a minimal response on cells devoid of the nanobody target (see FIGS. 2B and 2D, black curves). FIG. 3 shows clearly that the renilla luciferase activity is not induced upon stimulation of the co-culture with the nanobody-IFNα2R149A, indicating that the targeted IFN activity is delivered only on cells expressing the antigen recognized by the nanobody.

Figure 4A:
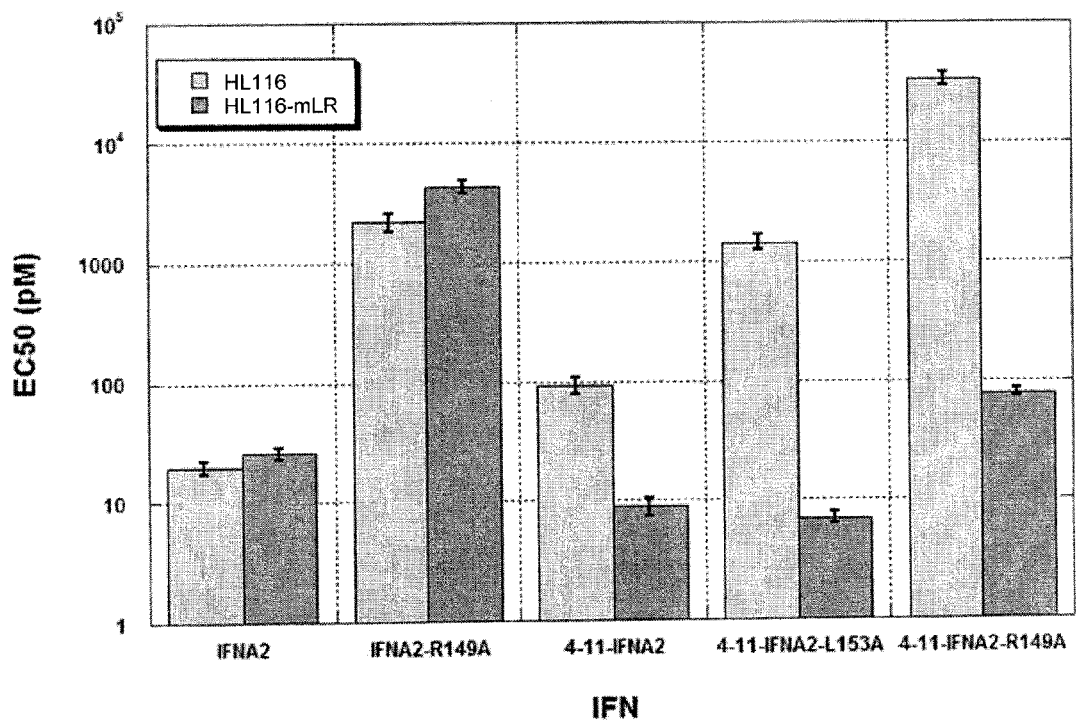
FIGS. 4A and 4B: Activity of the purified constructs targeting the mLR.
Figure 4B:
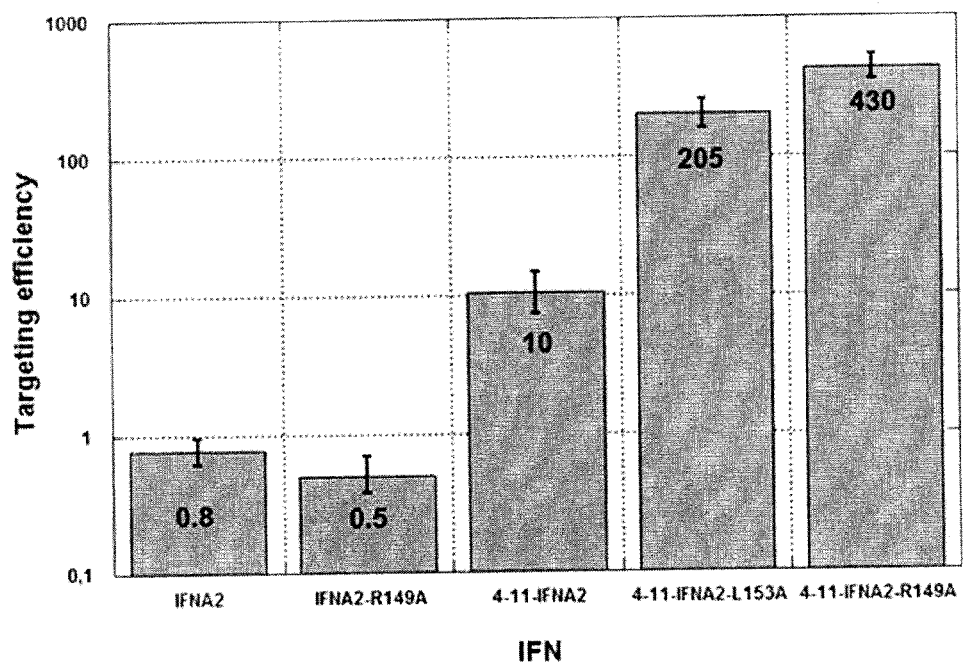

The efficacy of the targeting is further illustrated by comparing the activity of wild-type and two types of mutant IFN (L153A and R149A) when added to HL116 expressing or not expressing the murine leptin receptor that is used for the targeting. The results clearly show that the activity of the mutants is higher when the construct is targeted, and that the effect of targeting for the mutant is bigger than for wild-type (FIGS. 4A and 4B).

Figure 5:
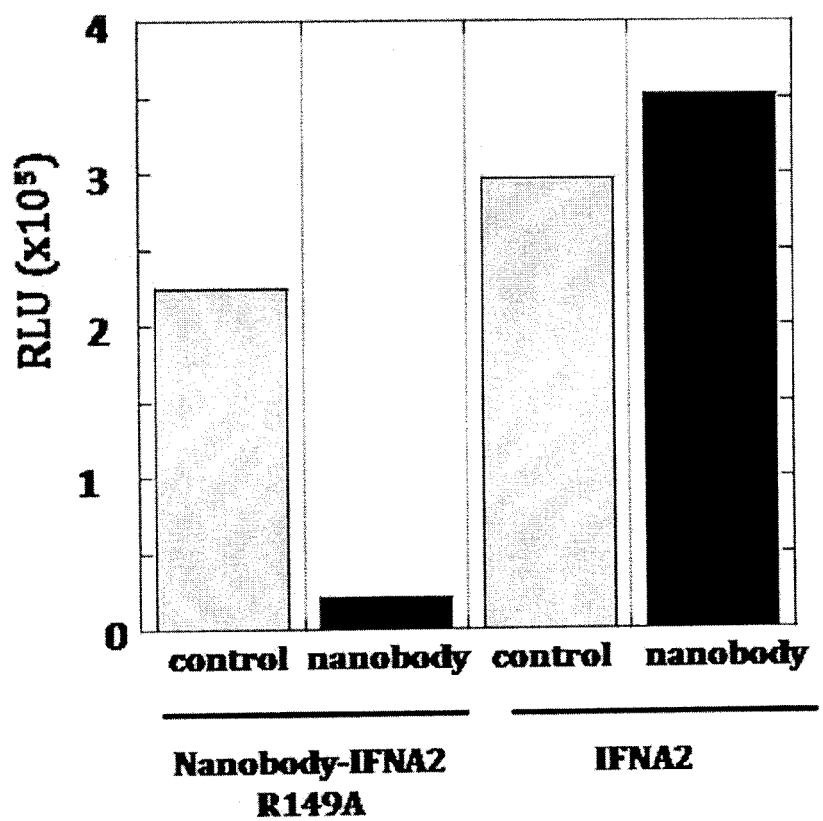
FIG. 5: Activity of the construct 4-11-IFNA2-R149A in presence and absence of the unconjugated leptin receptor binding nanobody. HL116 cells expressing the mLR were incubated for 6 hours with either the IFN-α2 (IFNA2) or the IFNA2-R149A fused to the nanobody 4-11 (Nanobody-IFNA2-R149A) at their respective EC50 concentration in the presence or absence (control) of a 100-fold molar excess of free 4-11 nanobody.

In order to prove that the targeting was nanobody specific, HL116 cells expressing the mLR were incubated for 6 hours with either the IFN-α2 (indicated as IFNA2) or the IFNA2-R149A fused to the nanobody 4-11 (Nanobody-IFNA2-R149A) at their respective EC50 concentration in the presence or absence (control) of a 100-fold molar excess of free 4-11 nanobody. Cells were lysed and the IFN-induced luciferase activities were measured. As shown in FIG. 5, the non-targeted IFN is not inhibited by the free nanobody, while the targeted construct is strongly inhibited, showing the specific effect of the targeting.

Figure 6:
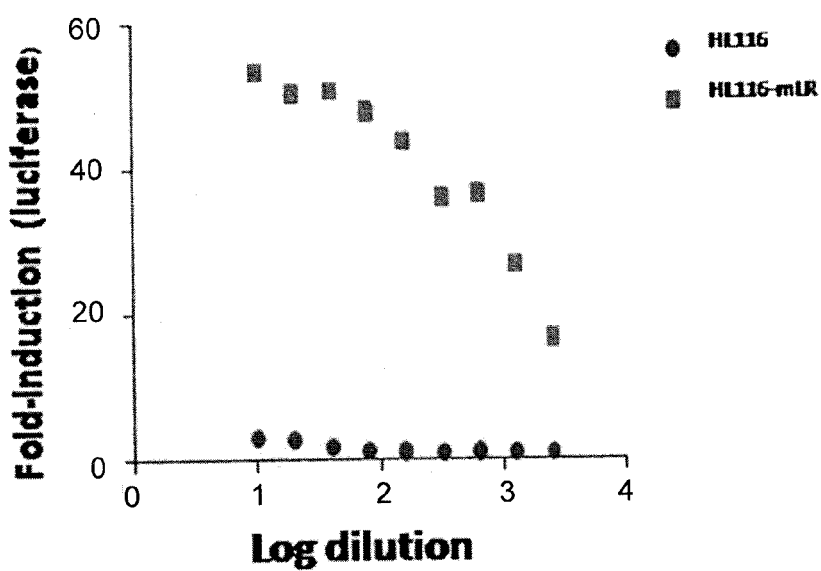
FIG. 6: Targeting the mutant IFN using the leptin binding nanobody 4-10.

The targeting to the leptin receptor is independent of the epitope on the receptor: using the anti-leptin receptor nanobody 4-10 (Zabeau et al., 2012), which recognizes a different domain on the receptor than the nanobody 4-11, a similar activation can be obtained using a targeted mutant IFN (FIG. 6).

Example 3

Figure 7:
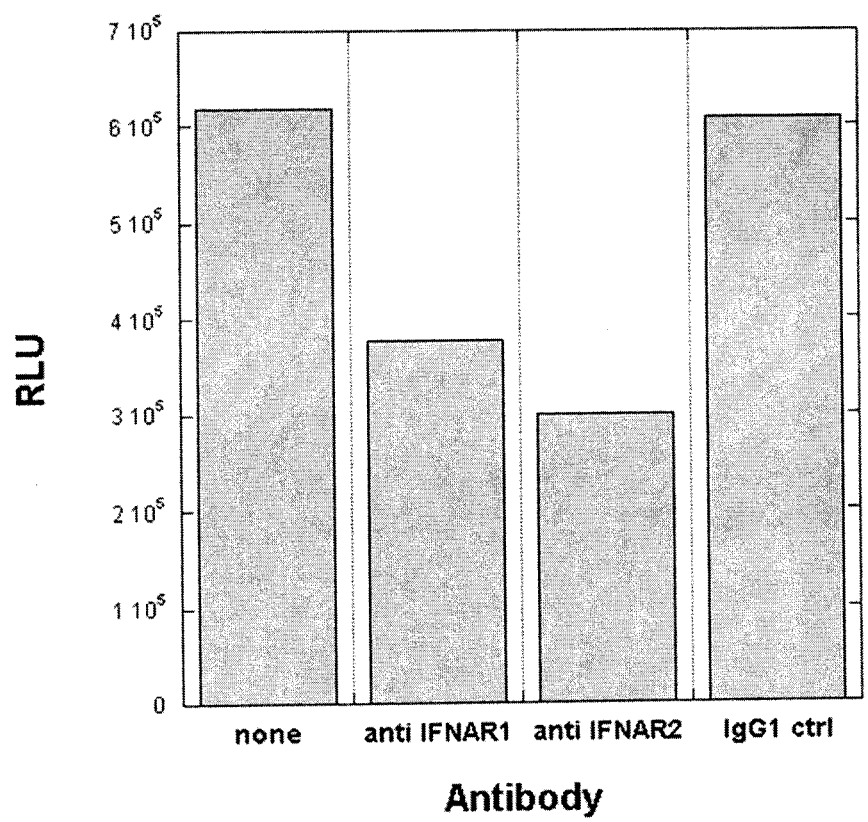
FIG. 7: Firefly luciferase activity induced in HL116 cells expressing the mLR by the nanobody-IFNα2R149A in the presence of anti IFNAR1 monoclonal antibody 64G12 (Benoit et al., J. Immunol. 150:707-716, 1993) or anti IFNAR2 monoclonal antibody MMHAR2 (PBL Interferon Source).

The IFN Activity of the Nanobody-IFN Fusion Proteins on Cells Expressing the Leptin Receptor is Mediated by Both IFN Receptor Chains In order to determine whether the IFN activity of the nanobody-IFN fusion proteins needs the activation of the IFN receptor, HL116 cells expressing the murine leptin receptor were pretreated with neutralizing antibodies against IFNAR1 or IFNAR2, and then stimulated with the nanobody-IFNA2-R149A fusion protein. The activity of the IFN-induced luciferase was measured. FIG. 7 shows that both anti-IFNAR1 and anti-IFNAR2 neutralizing antibodies inhibit the IFN activity of the nanobody-IFNA2-R149A.

Example 4

Figure 8A:
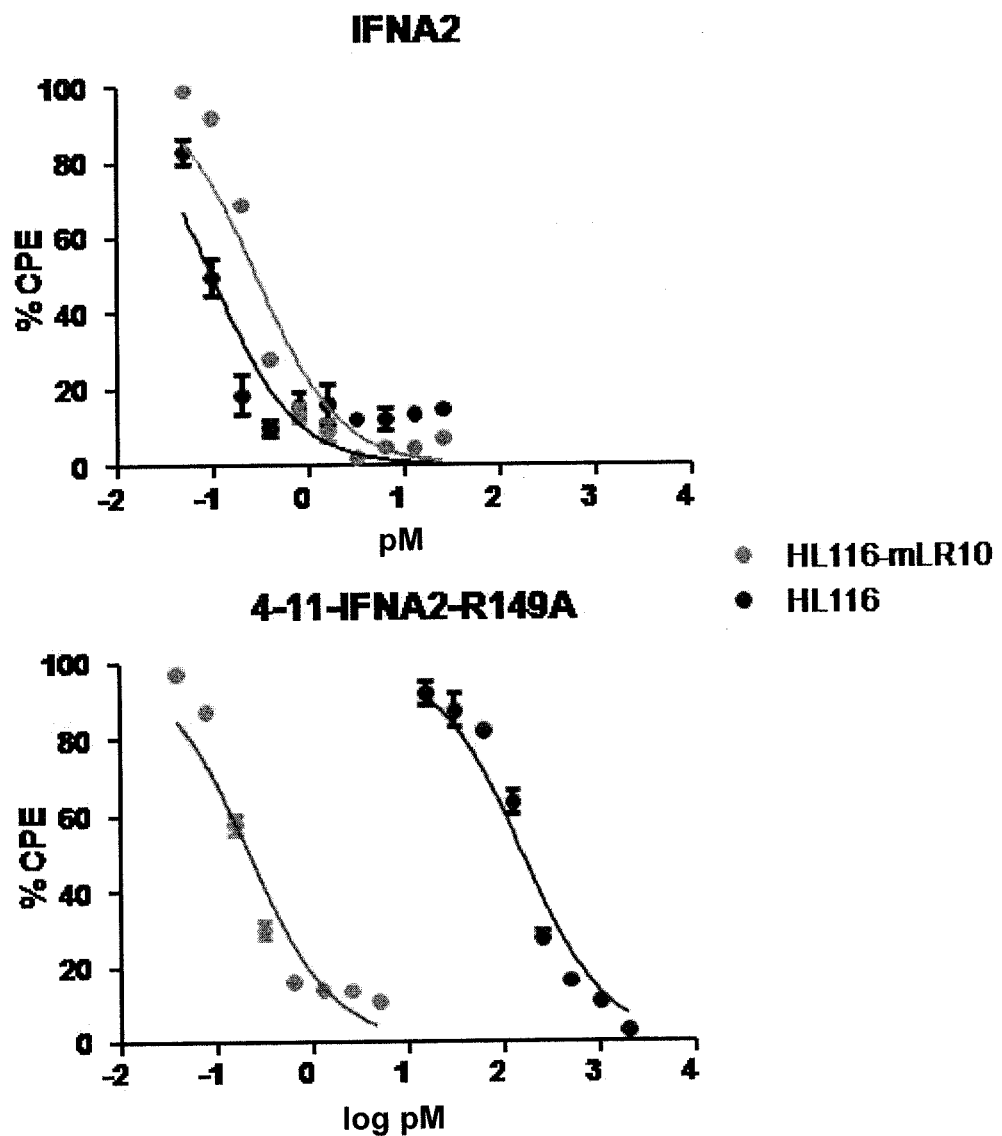
FIGS. 8A and 8B: Specificity of the targeting of 4-11-IFNA2-R149A to cells expressing the mLR.
Figure 8B:
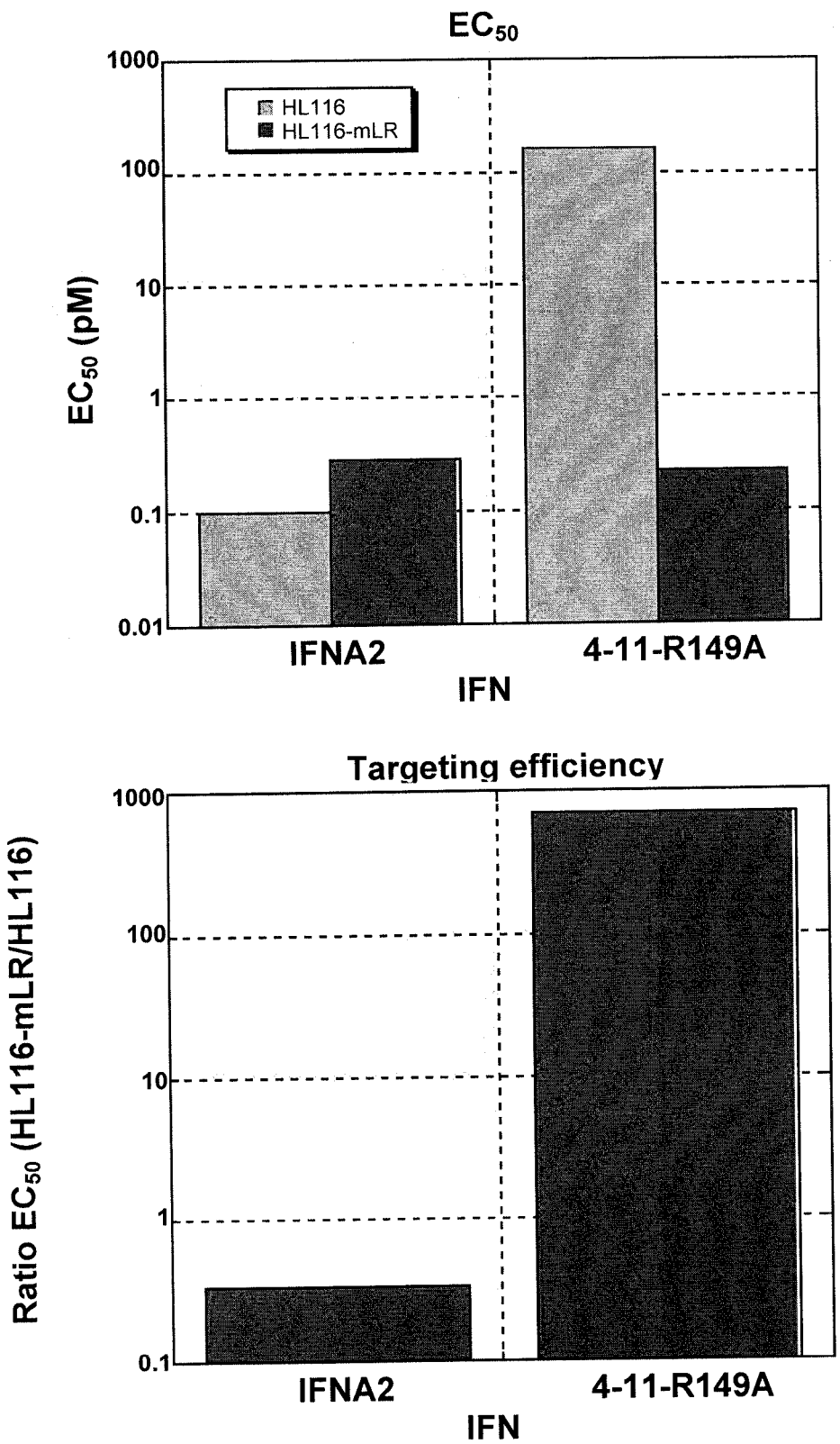

Target-Specific Induction of Antiviral Activity by 4-11-IFNA2-R149A in Cells Expressing the Murine Leptin Receptor Antiviral activity is an integrated part of the IFN response, implying the expression of several genes. Therefore, the antiviral activity on mLR-expressing cells was controlled, after targeting the mutant R149A IFN using the anti-leptin receptor antibody 4-11. The results are summarized in FIG. 8. The activity was measured as the cytopathic effect on HL116 cells, with or without leptin receptor expression. The specific antiviral activity of the 4-11-IFNA2-R149A nanobody-IFN fusion protein is 716-fold higher when assayed on leptin receptor-expressing cells compared to HL116 cells.

Example 5

Targeting of IFN Activity on Her2 Expressing Cells

In order to demonstrate that the concept is not restricted to cytokine receptor targeting, we generated similar fusion protein using the nanobody 2R5A against Her2 (Vaneycken et al., 2011) and the mutant IFN alpha2 R149A (2R5A-IFNA2-R149A). This molecule was assayed on BXPC3 (Pancreatic cancer, from ATCC) and BT474 (Breast cancer, from ATCC) cell lines and compared with the activity of IFN-α2 (IFNA2) for the induction of the 6-16 IFN-inducible gene as determined relative to GAPDH by quantitative RT-PCR. The BXPC3 and BT474 cells lines differ by their number of Her2 molecules expressed at their surface (10.9× $10^3$ and 478×$10^3$, respectively as reported by Gaborit et al. (2011)).

Figure 9A:
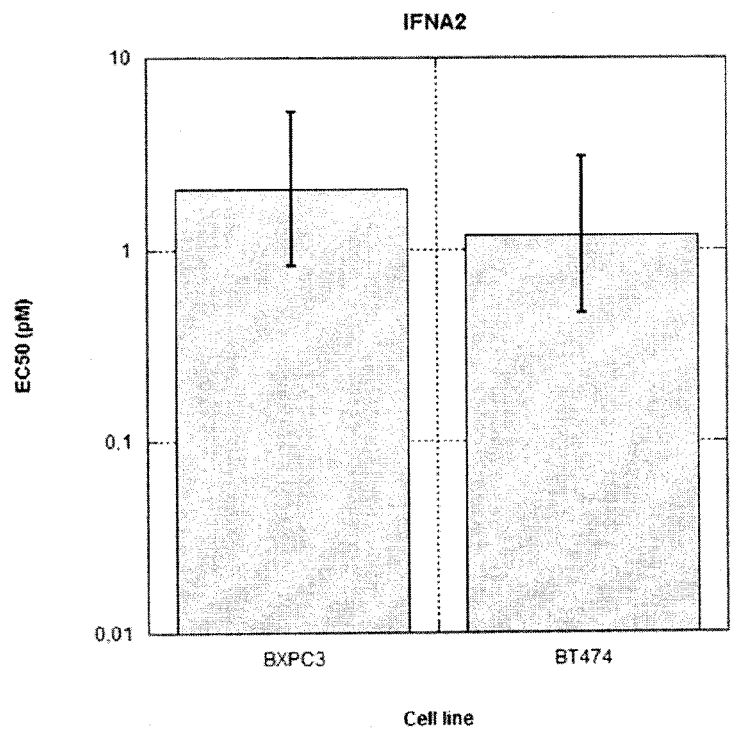
FIGS. 9A and 9B: Specific activities (EC50) of IFNα2 (FIG. 9A) and the nanobody-IFNα2R149A (2R5A.
Figure 9B:
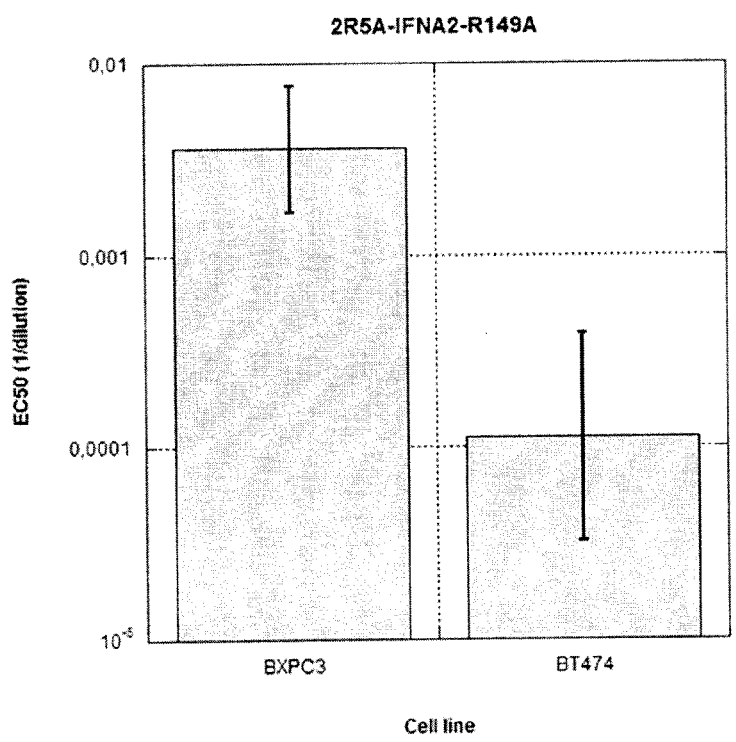

FIGS. 9A and 9B show the $EC_{50}$ determination of IFNA2 activity (FIG. 9A) and 2R5A-IFNA2-R149A activity (FIG. 9B) for the induction of the IFN-inducible gene 6-16 on BXPC3 and BT474 cell lines. FIG. 9A shows that BXPC3 and BT474 cell lines exhibit the same sensitivity to IFN-α2. FIG. 9B shows that the 2R5A-IFNA2-R149A nanobody-IFN fusion protein is much more potent on the BT474 cell line, which expresses 40-fold more Her2 molecule than BXPC3.

In conclusion, the concept that consists of targeting type I IFN activity on cells expressing a specific cell surface antigen, as shown on human cells expressing the mouse leptin receptor, can be extended to untransfected human cells expressing another cell surface molecule from a different structural family, at a level naturally found in several types of breast carcinoma.

Example 6

Targeting of Mutant IFNA2-Q149R to Mouse Cells Expressing Human Her2

Figure 10:
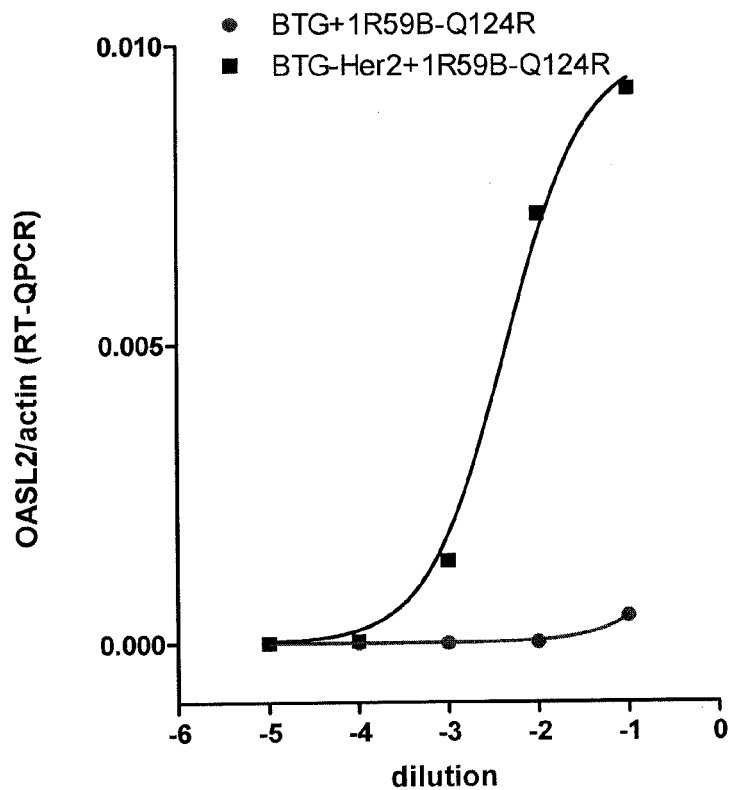
FIG. 10: Targeting of the 1R59B-IFNA2-Q124R to human Her2 expressing mouse cells. Quantification of the OASL2 mRNA expression in BTG9A cells with and without Her2 expression.

Mutant human IFNA2 Q149R was targeted to murine cells, expressing the human Her2, using the nanobody 1R59B in the 1R59B-IFNA2-Q124R. The IFNA2 Q124R has a high affinity for the murine IFNAR1 chain and a low activity for the murine IFNAR2 chain (Weber et al., 1987). The induction by IFN was measured as expression of the OASL2 messenger RNA, by RT-QPCR. The results are shown in FIG. 10. There is clearly a targeting-specific induction in the Her2-expressing cells, whereas there is no significant expression detected in untransfected BTG9A cells.

Figure 11:
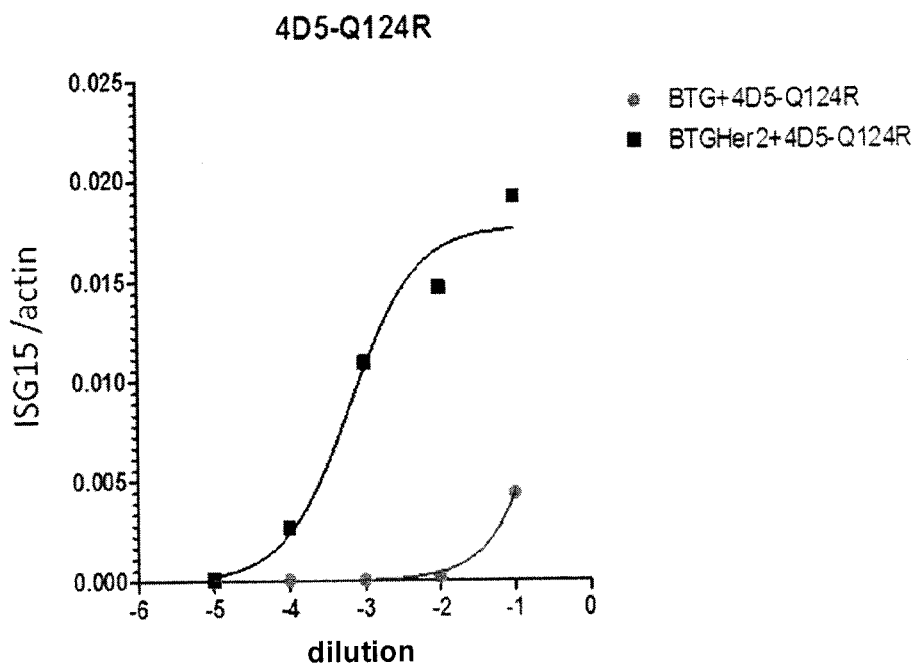
FIG. 11: Targeting of mutant IFNA2 to human Her2 expressing mouse cells, using a single chain antibody. Quantification of the ISG15 mRNA expression in BTG9A cells with and without Her2 expression.

Similar results were obtained when the Her2-specific ScFv against Her2 was used to target the mutant IFN Q124R. In this case, the IFN induction was measured using the ISG15 messenger RNA expression. The results are shown in FIG. 11. Again, a specific induction of ISG15 is seen in the cells expressing Her2, while there is little effect of the mutant IFN on the cells that do not express Her2.

Example 7

The Construct 1R59B-IFNA2-Q124R Does Not Activate the Phosphorylation of Her2

Figure 12:
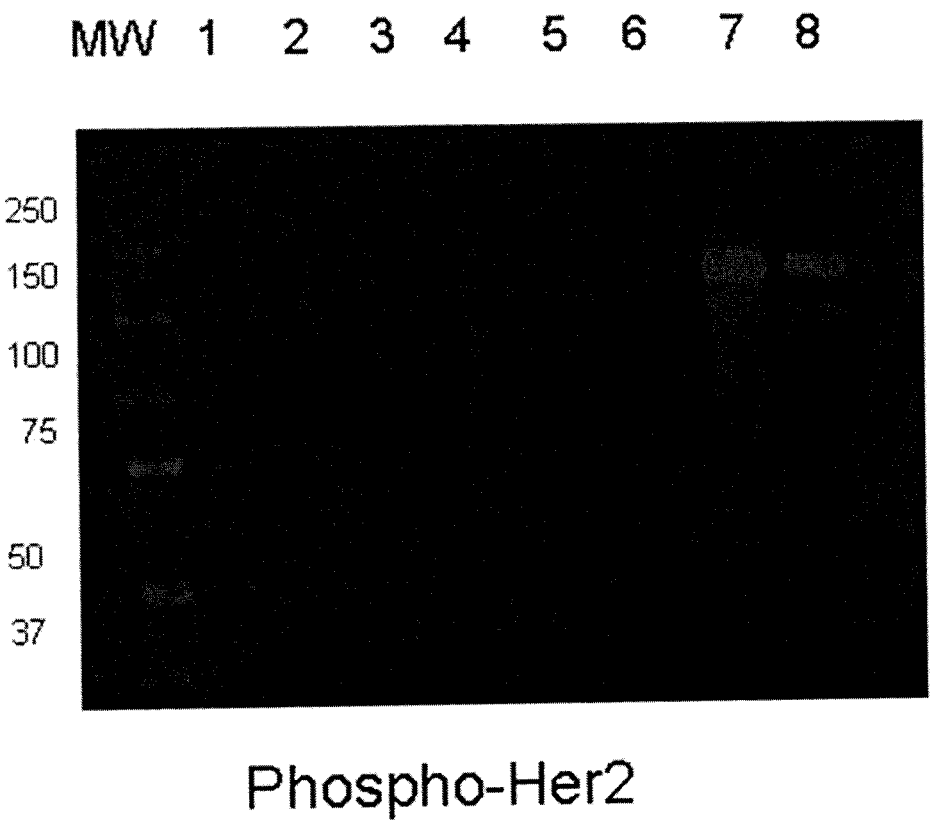
FIG. 12: Control of the activation of Her2 phosphorylation: Lanes 13 to 76: no phosphorylated Her2 in extract of BTG9A cells expressing human Her2 treated with different concentration (200 pM for lanes 3 to 5, 2 nM for lane 6) and time (lane 3: 5 minutes, lanes 4 and 6: 10 minutes, lane 5: 30 minutes) with the construct 1R59B-IFNA2-Q124R. Lanes 7 and 8: control for the detection of phosphorylated Her2 in the human BT474 cell line. Lane 1: extract of BTG9A cells. Lane 2: extract of BTG9A cells expressing human Her2.

To check whether targeting of Her2 is resulting in Her2 activation, Her2 phosphorylation was controlled in targeted cells. The results are shown in FIG. 12, clearly demonstrating that no phosphorylated Her2 could be detected in 1R59B-IFNA2-Q124R targeted cells, irrespective of the concentration or time of treatment.

Example 8

The Anti PD-L2 Nb122-IFNA2-Q124R Construct Activity is Targeted on Mouse Primary Cells Expressing PD-L2

Cells from a mouse peritoneal cavity were isolated and treated in vitro with Nb122-IFNA2-Q124R or natural mIFNα/β for 30 minutes. Cells were, fixed, permeabilized, labelled with antibodies against PD-L2 (APC) (BD #560086) and STAT1-PY701 (PE) (BD #612564) and analyzed by FACS.

The PD-L2-positive cell population represents 20% of the total cell population present in the mouse peritoneal cavity.

Figure 13:
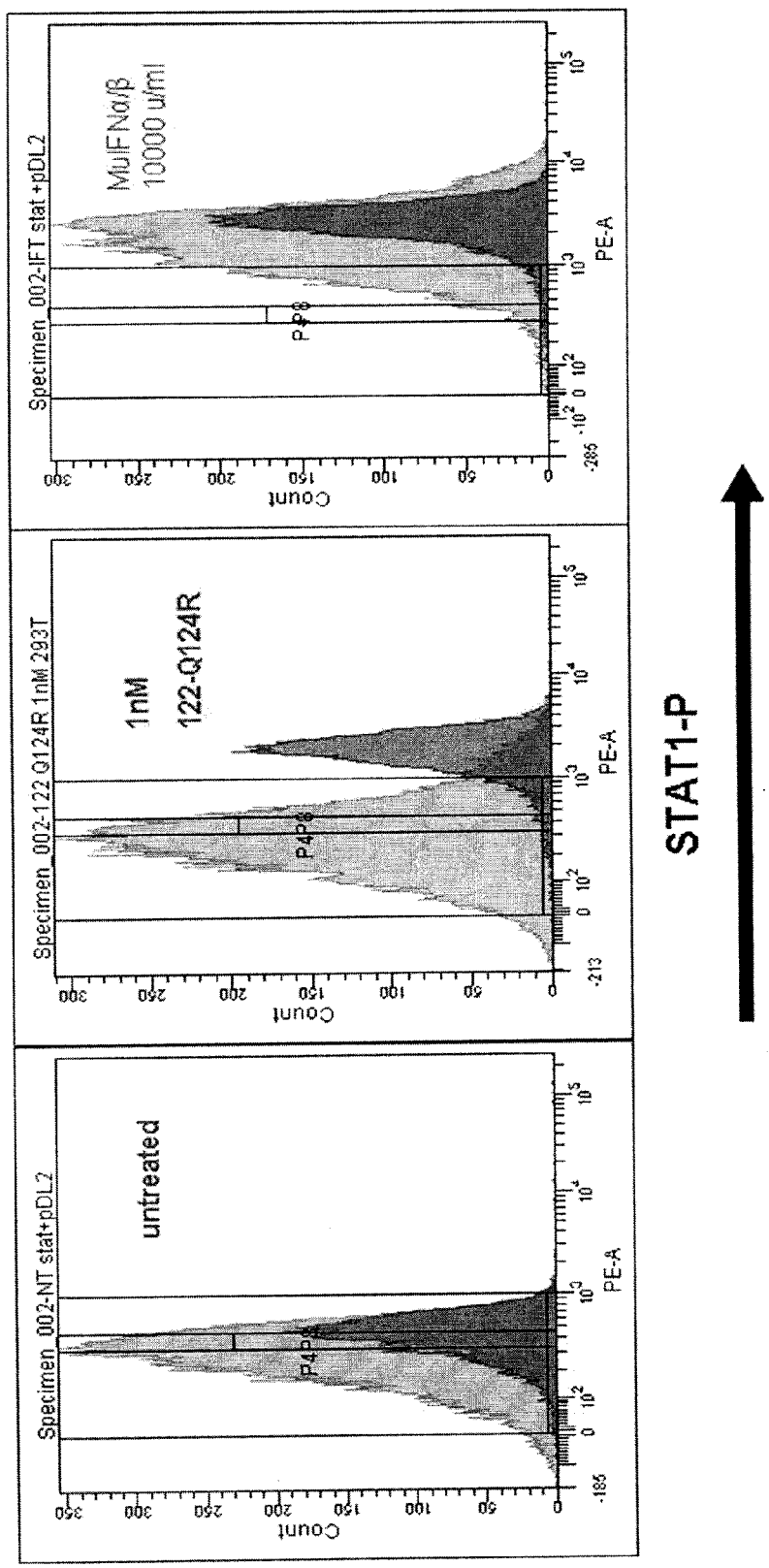
FIG. 13: Targeting the anti-PD-L2 122-IFNA2-Q124R to mouse primary cells endogenously expressing PD-L2. The activation is measured as STAT phosphorylation. The light gray area represents the PD-L2-negative cell population; the dark gray area represents the PD-L2-positive population.

The results are shown in FIG. 13. It is clear from this figure that in untreated cells, or in non-targeted, murine IFN-treated cells, the peaks of STAT1-P for PD-L2 expressing and non-expressing cells coincide. Moreover, a clear induction in STAT1-P can be seen by murine IFN treatment. Treatment with the targeted mutant IFN, however, results in a specific shift in the STAT1-P only for the PD-L2 expressing cells.

The same result is obtained if the IFN response of splenocytes is analyzed in a similar experiment. The PD-L2-positive cell population represents 1% of the total cell population present in mouse spleen, indicating that also a minor cell population can be targeted in an efficient way.

Example 9

Figure 14:
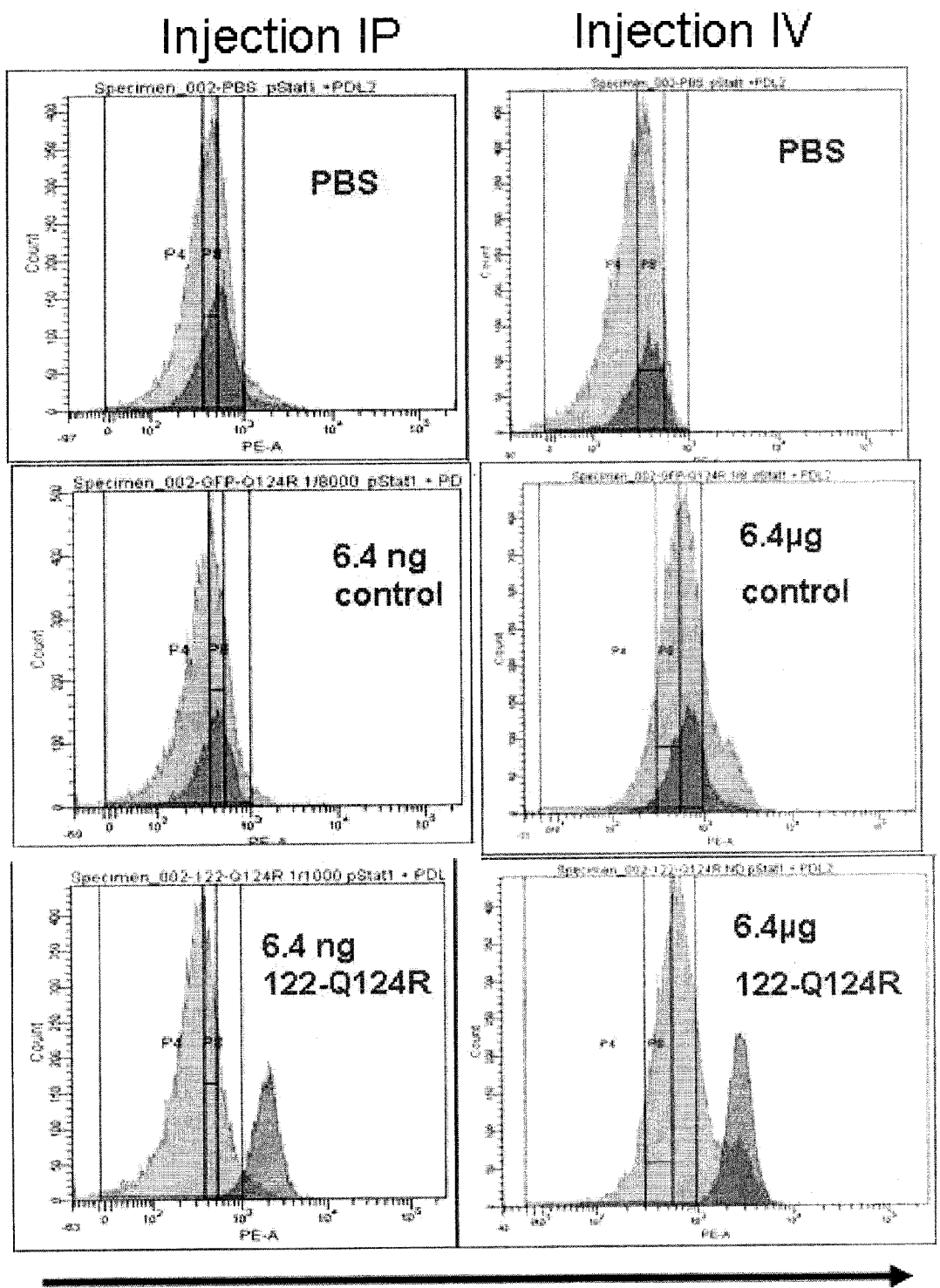
FIG. 14: In vivo targeting of 122-IFNA2-Q124R to PD-L2 expressing cells. Mice were injected intraperitoneally (IP) or intravenous (IV) with either PBS, a control construct (nanobody against GFP fused to mutant IFNA2-Q124R, indicated as control) or a targeted mutant IFN (targeted to PD-L2, Nb122-IFN2-Q124R, indicated as 122-Q124R. The light gray area represents the PD-L2-negative cell population; the dark gray area represents the PD-L2-positive population.

In Vivo Injection of 122-IFNA2-Q124R Construct Induces an IFN Response Only in PD-L2-Expressing Cells Mice were injected (IP or IV) with either PBS, Nb122-IFNA2-Q124R or a control Nb (against GFP) fused to IFNA2-Q124R. 30 min post injection, mice were killed, cells from the peritoneal cavity were recovered by washing the peritoneal cavity with PBS, fixed (PHOSFLOW (flow cytometry-based protein phosphorylation detection) Fix buffer I BD #557870), permeabilized (PHOSFLOW (flow cytometry-based protein phosphorylation detection) Perm buffer III, BD #558050), labelled with Abs against PD-L2 (APC) (BD #560086) and STAT1-PY701 (PE) (BD #612564) and analysed by FACS. The results are shown in FIG. 14. STAT1-P coincides in PD-L2 positive and negative cells treated with either PBS or control nanobody. However, a clear induction in STAT1-P (only in the PDL2 positive cell population) can be seen when the mice are injected with the targeted mutant IFN.

As a control, STAT1-P was checked in mice, iv injected with different doses of natural mouse IFN (10,000, 100,000 or 1,000,000 units), and no difference in STAT1-P could be detected between the PD-L2-positive and PD-L2-negative cells.

Figure 15:
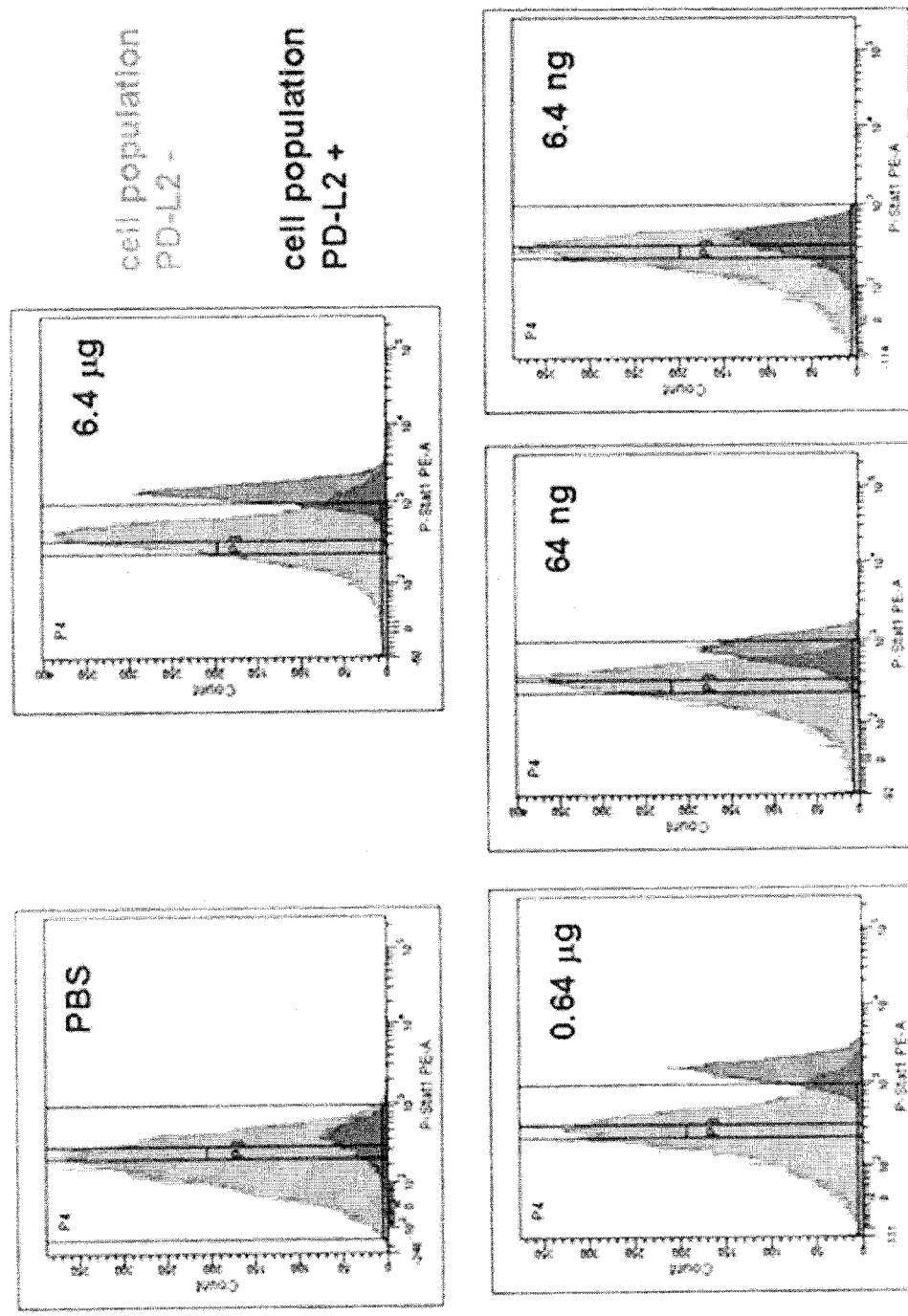
FIG. 15: Dose response curve after IV injection of 122-IFN-Q124R in mice. The light gray area represents the PD-L2-negative cell population; the dark gray area represents the PD-L2-positive population.
Figure 16:
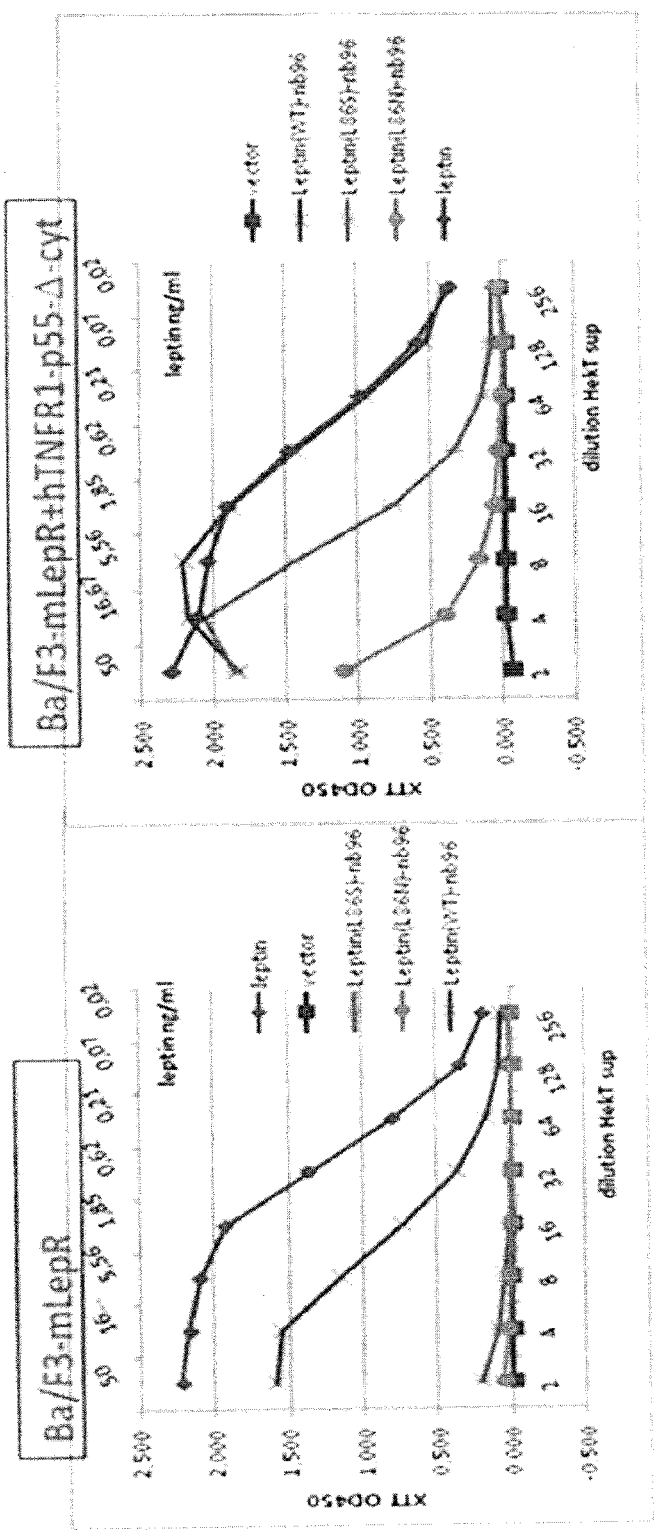
FIG. 16: Leptin-dependent growth induced by targeted mutant leptin: the loss in activity of a mutant leptin can be rescued in Ba/F3 cells expressing the human TNFR1. First two panels, experiment using the H6-leptin construct; second two panels, experiment using the mleptin construct. H6 indicated the his tag (6×his).

FIG. 15 shows a similar dose response curve after iv injection of the Nb122-IFNA2-Q124R construct. A shift in STAT1-P in the PD-L2 expressing cells can be noticed even at the lowest dose of 64 ng.

Example 10

Targeting of Mutant Leptin to the Leptin Receptor, Using a Truncated TNFα Receptor Ba/F3 cells are growth-dependent on IL-3. After transfection with the mLR, Ba/F3 cells also proliferate with leptin. Leptin mutants with reduced affinity for their receptor are less potent in inducing and sustaining proliferation of Ba/F3-mLR cells. Leptin mutant L86S has a moderate, and mutant L86N has a strong, reduction in affinity and, hence, a moderate and strong reduced capacity to induce proliferation, respectively.

Additional transfection of Ba/F3-mLR cells with the human TNFα Receptor 1 (hTNFR1) lacking its intracellular domain introduces a non-functional receptor, which can function as a membrane-bound extracellular marker.

Chimeric proteins consisting of leptin and a nanobody against human TNFR1 (here nb96) will bind to cells carrying the mLR and to cells carrying the hTNFR1. Chimeric proteins with leptin mutants L86S and L86N have reduced affinity for the LR but retain their affinity for the hTNFR1.

Chimeric proteins were produced by transient transfection of Hek293T cells with expression plasmids. Supernatant was 0.45 μm filtered and serially diluted in 96-well plates for the assay. A serial dilution of purified recombinant leptin was used as a reference. 3000 to 10000 cells were plated per well and proliferation was measured by staining with XTT four or five days later. OD was measured at 450 nm. The results are shown in FIG. 16, for two experiments using a different leptin construct (see FIG. 17). For both constructs, an hTNFR depending growth stimulation can be seen for the mutant constructs, whereas the hTNFR expression does not affect the growth of the cells treated with wt (non-targeted) leptin. It is clear from these results that the targeting can compensate for the negative effect of the mutation.

REFERENCES

Abraham, A. K., M. Ramanathan, B. Weinstock-Guttman, and D. E. Mager (2009). *Biochemical Pharmacology* 77:1757-1762.

Benoit, P., D. Maguire, I. Plavec, H. Kocher, M. Tovey, and F. Meyer (1993). *J. Immunol.* 150:707-716.

Blake, A. W., L. McCartney, J. Flint, D. N. Bolam, A. B. Boraston, H. J. Gilbert, and J. P. Knox (2006). *J. Biol. Chem.* 281:29321-29329.

Bourachot, B., J. Jouanneau, I. Giri, M. Katinka, S. Cereghini, and M. Yaniv (1982). *EMBO J.* 1:895-900.

Brecht, A., G. Gauglitz, and J. Polster (1993). *Biosens. Bioelectron.* 8:387-392.

Coccia, E. M., M. Severa, E. Giacomini, D. Monneron, M.-E. Remoli, I. Julkunen, M. Cella, R. Lande, and G. Uzé (2004). *Eur. J. Immunol.* 34:796-805.

Conklin, D. (2004). *J. Computational Biol.* 11:1189-1200.

Dimitrov, D. S. (2009). *mAbs* 1:26-28.

Eyckerman, S., W. Waelput, A. Verhee, D. Broekaert, J. Vendekerckhove, and J. Tavernier (1999). *Eur. Cytok. Netw.* 10:549-559.

Gaborit, N., C. Labouret, J. Vallaghe, F. Peyrusson, C. Bascoul-Mollevi, E. Crapez, D. Azria, T. Chardès, M. A. Poul, G. Mathis, H. Bazin, and A. Pélegrin (2011). *J. Biol. Chem.* 286:11337-11345.

Ortiz-Sanchez, E., G. Helguera, T. R. Daniels, and M. L. Penichet (2008). *Expert Opin. Biol. Ther.* 8:609-632.

Pellegrini, S., J. John, M. Shearer, I. M. Kerr, and G. R. Stark (1989). *Mol. Cell. Biol.* 9:4605-4012.

Piehler, J., L. C. Roisman, and G. Schreiber (2000). *J. Biol. Chem.* 275:40425-40433.

Lasfargues, E. Y., W. G. Coutino, and A. S. Dion (1979). *In Vitro* 15:723-729.

Nygren, P. A. (2008). *FEBS J.* 275:2668-2676.

Roisman, L. C., J. Piehler, J. Y. Trosset, H. A. Scheraga, and G. Schreiber (2001). *Proc. Natl. Acad. Sci. USA* 98:13231-13236.

Rossi, E. A., D. M. Goldenberg, T. M. Cardillo, R, Stein and C. H. Chang (2009) *Blood* 114:3964-3871.

Southern, P. J. and P. Berg (1982). *J. Mol. Appl. Genet.* 1:327-341.

Skerra, A. (2008). *FEBS J.* 275:2677-2683.

Stewart II W. E. *The Interferon System*, Springer-Verlag, Wien, N.Y. 1979.

Stumpp, M. T., H. K. Binz, and P. Amstutz (2008). *Drug Discov. Today* 13:695-701.

Takabe, Y., M. Seiki, J. Fujisawa, P. Hoy, K. Yokata, and N. Arai (1988). *Mol. Cell. Biol.* 8:466-472.

Tan, M. H., N. J. Nowak, R. Loor, H. Ochi, A. A. Sandberg, C. Lopez, J. W. Pickren, R. Berjian, H. O. Douglass, Jr., and T. M. Chu (1986). *Cancer Invest.* 4:15-23.

Tramontano, A., E. Bianchi, S. Venturini, F. Martin, A. Pessi, and M. Sollazzo (1994). *J. Mol. Recognition* 7:9-24.

Uzê et al. (1990). *Cell* 60:225-234.

Uzê, G., S. Di Marco, E. Mouchel-Veilh, D. Monneron, M. T. Bandu, M. A. Horisberger, A. Dorques, G. Lutfalla, and K. E. Mogensen (1994). *J. Mol. Biol.* 243:245-257.

Vaneycken, I., N. Devoogdt, N. Van Gassen, C. Vincke, C. Xavier, U. Wernery, S. Muyldermans, T. Lahoutte, and V. Caveliers (2011). *FASEB J.* 25:2433-2446.

Weber et al. (1987). *EMBO J.* 6:591-598.

Wörn et al. (1998). *FEBS Lett.* 427:357-361.

Zabeau, L., A. Verhee, D. Catteeuw, L. Faes, S. Seeuws, T. Decruy, D. Elewaut, F. Peelman, and J. Tavernier (2012). *Biochem. J.* 441:425-434.

The invention claimed is:

1. A composition comprising a targeting construct, the targeting construct comprising: mutated human interferon alpha 2, said mutated human interferon alpha 2 having a R149A mutation and a reduced affinity as compared to the wild type human interferon alpha 2, and a targeting moiety, said targeting moiety comprises an antibody directed to a programmed death-ligand 2 (PD-L2), wherein the targeting moiety restores the reduced affinity of the mutated human interferon alpha 2 for IFNAR2 on targeted cells.

2. The targeting construct according to claim 1, wherein said antibody is a nanobody.

3. A pharmaceutical composition comprising a targeting construct, the targeting construct comprising:

the composition according of claim 1; and a suitable excipient.

4. The composition of claim 1, further comprising a linker wherein the mutated human interferon alpha 2 and the targeting moiety are connected via a linker.

* * * * *

UNITED STATES PATENT AND TRADEMARK OFFICE
CERTIFICATE OF CORRECTION

PATENT NO. : 9,492,562 B2  
APPLICATION NO. : 14/372730  
DATED : November 15, 2016  
INVENTOR(S) : Jan Tavernier et al.

It is certified that error appears in the above-identified patent and that said Letters Patent is hereby corrected as shown below:

In the Claims

In Claim 1, Column 21, Line 22, add "for IFNAR2" after --a reduced affinity--.

Signed and Sealed this  
Third Day of January, 2017

Michelle K. Lee  
*Director of the United States Patent and Trademark Office*

SEQUENCE LISTING

```
<160> NUMBER OF SEQ ID NOS: 10

<210> SEQ ID NO 1
<211> LENGTH: 108
<212> TYPE: DNA
```

<213> ORGANISM: Artificial Sequence
<220> FEATURE:
<223> OTHER INFORMATION: Primer

<400> SEQUENCE: 1 gggggtccg gaccatcacc atcaccatca ccatcaccat caccctgctt ctcccgcctc    60
cccagcatca cctgccagcc cagcaagtga tagcctggaa tttattgc               108

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
cgtctagatc attccttact tcttaaac                                     28

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cacgactgta ggccccagcg a                                            21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
agcagctgtc tctcccctcc g                                            21

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
agagggaaat cgtgcgtgac                                              20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
caatagtgat gacctggccg t                                            21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7

```
gagctagagc ctgcagcaat                                                       20
```

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8

```
ttctgggcaa tctgcttctt                                                       20
```

<210> SEQ ID NO 9
<211> LENGTH: 352
<212> TYPE: PRT
<213> ORGANISM: Artificial Sequence
<220> FEATURE:
<223> OTHER INFORMATION: H6-Leptin construct
<220> FEATURE:
<221> NAME/KEY: MISC_FEATURE
<222> LOCATION: (94)..(94)
<223> OTHER INFORMATION: Xaa can be Ser or Asn

<400> SEQUENCE: 9

```
His His His His His His Gly Gly Ser Gly Ile Gln Lys Val Gln Asp
1               5                   10                  15

Asp Thr Lys Thr Leu Ile Lys Thr Ile Val Thr Arg Ile Asn Asp Ile
            20                  25                  30

Ser His Thr Gln Ser Val Ser Ala Lys Gln Arg Val Thr Gly Leu Asp
        35                  40                  45

Phe Ile Pro Gly Leu His Pro Ile Leu Ser Leu Ser Lys Met Asp Gln
    50                  55                  60

Thr Leu Ala Val Tyr Gln Gln Val Leu Thr Ser Leu Pro Ser Gln Asn
65                  70                  75                  80

Val Leu Gln Ile Ala Asn Asp Leu Glu Asn Leu Arg Asp Xaa Leu His
                85                  90                  95

Leu Leu Ala Phe Ser Lys Ser Cys Ser Leu Pro Gln Thr Ser Gly Leu
            100                 105                 110

Gln Lys Pro Glu Ser Leu Asp Gly Val Leu Glu Ala Ser Leu Tyr Ser
        115                 120                 125

Thr Glu Val Val Ala Leu Ser Arg Leu Gln Gly Ser Leu Gln Asp Ile
    130                 135                 140

Leu Gln Gln Leu Asp Val Ser Pro Glu Cys Ala Leu Asp Gly Gly Ser
145                 150                 155                 160

Gly Gly Ser Gly Gly Ser Gly Gly Ser Gly Gly Ser Gly Gly Ser Gly
                165                 170                 175

Gly Ser Gly Gly Ser Gly Gly Ser Gly Gly Ser Gly Gly Ser Gly Gly
            180                 185                 190

Ser Gly Gly Ser Gly Gly Ser Gly Gly Ser Gly Gly Ser Gly Gly Ser
        195                 200                 205

Gly Gly Ser Gly Gly Ser Gly Gly Ser Gly Ser Met Ala Gln Val
    210                 215                 220

Gln Leu Gln Glu Ser Gly Gly Gly Val Val Gln Pro Gly Gly Ser Leu
225                 230                 235                 240

Thr Leu Ser Cys Thr Arg Thr Gly Phe Thr Ala Ser Thr Asn Ala Val
                245                 250                 255

Gly Trp Tyr Arg Gln Gly Pro Gly Lys Lys Cys Glu Trp Val Ser Tyr
            260                 265                 270
```

-continued

```
Met Thr Ile Pro Ser Gly Arg Thr Thr Tyr Ala Asp Ala Val Lys Gly
            275                 280                 285

Arg Phe Ala Met Ser Arg Asp Lys Ala Lys Ser Thr Val Phe Leu Gln
290                 295                 300

Met Asn Ser Leu Lys Pro Glu Asp Thr Ala Val Tyr Tyr Cys Gly Asp
305                 310                 315                 320

Val Pro Phe Ser Thr Leu Pro Ala Met Cys Thr Asn Asp Gly Pro Trp
                325                 330                 335

Gly Gln Gly Thr Gln Val Thr Val Ser Ser His His His His His His
                340                 345                 350
```

<210> SEQ ID NO 10
<211> LENGTH: 345
<212> TYPE: PRT
<213> ORGANISM: Artificial Sequence
<220> FEATURE:
<223> OTHER INFORMATION: Mleptin construct
<220> FEATURE:
<221> NAME/KEY: MISC_FEATURE
<222> LOCATION: (88)..(88)
<223> OTHER INFORMATION: Xaa can be Ser or Asn

<400> SEQUENCE: 10

```
Gly Gly Ser Gly Ile Gln Lys Val Gln Asp Asp Thr Lys Thr Leu Ile
1               5                   10                  15

Lys Thr Ile Val Thr Arg Ile Asn Asp Ile Ser His Thr Gln Ser Val
                20                  25                  30

Ser Ala Lys Gln Arg Val Thr Gly Leu Asp Phe Ile Pro Gly Leu His
            35                  40                  45

Pro Ile Leu Ser Leu Ser Lys Met Asp Gln Thr Leu Ala Val Tyr Gln
    50                  55                  60

Gln Val Leu Thr Ser Leu Pro Ser Gln Asn Val Leu Gln Ile Ala Asn
65                  70                  75                  80

Asp Leu Glu Asn Leu Arg Asp Xaa Leu His Leu Leu Ala Phe Ser Lys
                85                  90                  95

Ser Cys Ser Leu Pro Gln Thr Ser Gly Leu Gln Lys Pro Glu Ser Leu
            100                 105                 110

Asp Gly Val Leu Glu Ala Ser Leu Tyr Ser Thr Glu Val Val Ala Leu
        115                 120                 125

Ser Arg Leu Gln Gly Ser Leu Gln Asp Ile Leu Gln Gln Leu Asp Val
    130                 135                 140

Ser Pro Glu Cys Ala Leu Asp Gly Gly Ser Gly Gly Ser Gly Gly Ser
145                 150                 155                 160

Gly Gly Ser Gly Gly Ser Gly Gly Ser Gly Gly Ser Gly Gly Ser Gly
                165                 170                 175

Gly Ser Gly Gly Ser Gly Gly Ser Gly Gly Ser Gly Gly Ser Gly Gly
            180                 185                 190

Ser Gly Gly Ser Gly Gly Ser Gly Gly Ser Gly Gly Ser Gly Gly Ser
    195                 200                 205

Gly Gly Ser Ser Gly Ser Met Ala Gln Val Gln Leu Gln Glu Ser Gly
210                 215                 220

Gly Gly Val Val Gln Pro Gly Gly Ser Leu Thr Leu Ser Cys Thr Arg
225                 230                 235                 240

Thr Gly Phe Thr Ala Ser Thr Asn Ala Val Gly Trp Tyr Arg Gln Gly
                245                 250                 255

Pro Gly Lys Lys Cys Glu Trp Val Ser Tyr Met Thr Ile Pro Ser Gly
```

-continued

```
            260                 265                 270

Arg Thr Thr Tyr Ala Asp Ala Val Lys Gly Arg Phe Ala Met Ser Arg
        275                 280                 285

Asp Lys Ala Lys Ser Thr Val Phe Leu Gln Asn Ser Leu Lys Pro Glu
    290                 295                 300

Asp Thr Ala Val Tyr Tyr Cys Gly Asp Val Pro Phe Ser Thr Leu Pro
305                 310                 315                 320

Ala Met Cys Thr Asn Asp Gly Pro Trp Gly Gln Gly Thr Gln Val Thr
                325                 330                 335

Val Ser Ser His His His His His His
            340                 345
```